US008093263B2

(12) United States Patent
Gatti McArthur et al.

(10) Patent No.: US 8,093,263 B2
(45) Date of Patent: Jan. 10, 2012

(54) SUBSTITUTED PYRAZOLO [1,5-A] PYRIMIDINES AS METABOTROPIC GLUTAMATE ANTAGONISTS

(75) Inventors: Silvia Gatti McArthur, Basel (CH); Erwin Goetschi, Reinach (CH); Juergen Wichmann, Steinen (DE); Thomas Johannes Woltering, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 451 days.

(21) Appl. No.: 12/348,962

(22) Filed: Jan. 6, 2009

(65) Prior Publication Data

US 2009/0143580 A1  Jun. 4, 2009

Related U.S. Application Data

(62) Division of application No. 11/524,135, filed on Sep. 20, 2006, now Pat. No. 7,504,404.

(30) Foreign Application Priority Data

Sep. 27, 2005 (EP) ..................................... 05108910

(51) Int. Cl.
C07D 471/04 (2006.01)
A61K 31/519 (2006.01)
A61K 31/437 (2006.01)
A61P 25/28 (2006.01)
A61P 25/16 (2006.01)
A61P 25/18 (2006.01)

(52) U.S. Cl. ...... 514/299; 546/121; 544/281; 514/259.3
(58) Field of Classification Search .................. 546/121; 514/299
See application file for complete search history.

(56) References Cited

U.S. PATENT DOCUMENTS

| 3,725,428 A | 4/1973 | Janiak |
| 4,028,374 A | 6/1977 | Pelosi, Jr. et al. |
| 5,099,021 A | 3/1992 | Worther et al. |
| 6,878,720 B2 | 4/2005 | Altmann et al. |
| 2003/0139426 A1 | 7/2003 | Wilde et al. |

FOREIGN PATENT DOCUMENTS

| DE | 1 953 149 | 5/1970 |
| EP | 0 199 400 A | 10/1986 |
| EP | 295 656 | 12/1988 |
| EP | 0343893 | 11/1989 |
| EP | 0404440 A | 12/1990 |
| EP | 427 963 | 5/1991 |
| EP | 0604657 | 7/1994 |
| EP | 0 891 978 A2 | 1/1999 |
| FR | 2 753 970 A | 4/1998 |
| GB | 1 345 552 A | 1/1974 |
| GB | 1 538 822 A | 1/1979 |
| WO | WO 97/29109 A1 | 8/1997 |
| WO | WO 99/24035 | 5/1999 |
| WO | WO 99/37630 | 7/1999 |
| WO | WO 00/18767 | 4/2000 |
| WO | WO 00/27819 A | 5/2000 |
| WO | WO 01//19360 A2 | 9/2000 |
| WO | WO 01/97786 | 12/2001 |
| WO | WO 02/083652 | 10/2002 |
| WO | WO 02/092086 | 11/2002 |
| WO | WO 03/048132 A2 | 6/2003 |
| WO | WO 03/049741 | 6/2003 |
| WO | WO 03/053946 | 7/2003 |
| WO | WO 03/066623 A1 | 8/2003 |
| WO | WO 2004/092135 | 10/2004 |
| WO | WO 2004/111040 | 12/2004 |
| WO | WO 2005/040171 | 5/2005 |
| WO | WO 2005/041971 A1 | 5/2005 |
| WO | WO 2005/123738 | 12/2005 |

OTHER PUBLICATIONS

D'Onofrio, et al., J. Neurochem. (Mar. 2003) vol. 84(6) pp. 1288-1295.
Database Chemcats Online, Chemical Abstract Service, Columbus, Ohio, US, XP002316354, Apr. 5, 2005.
Fraley et al., Bioorg. Med. Chem. Lett., 12, pp. 3537-3541 (2002).
Poulsen, et al., Bioorganic & Medicinal Chemistry, vol. 6 (1998) pp. 619-641.
Müller, et al., Bioorganic & Medicinal Chemistry, vol. 6, (1998) pp. 707-719.
Kim, et al., J. Med. Chem., (1998), vol. 41, pp. 2835-2845.
Li, et al., J. Med. Chem., (1998), vol. 41, pp. 3186-3201.
Baraldi, et al., J. Med. Chem., (1998), vol. 41, pp. 2126-2133.
Li, et al., J. Med. Chem., (1999), vol. 42, pp. 706-721.
Baraldi, et al., J. Med. Chem., (1996), vol. 39, pp. 1164-1171.
Colotta, et al., Arch. Pharm. Pharm. Med. Chem., vol. 332, pp. 39-41 (1999).
Auchampach, et al., Am. J. Physiol. vol. 276, H1113-1116 (1999).
Haas, et al., Naunyn-Schmiedeberg's, Arch. Pharmacol. vol. 362, pp. 375-381 (2000).
Patent Abstracts of Japan, vol. 1999, No. 10, JP 11 130761a.
Pandeya, S. N. et al., Indian Drugs (1985), 23(3), 146-51.
Daidone, G. et al., Il Farmaco vol. 44, No. 5 (1989), pp. 465-473.
The Merck Index 12th Ed. (1996) p. 506.
Abstract corresponding to FR 2 753 970 (B13), Apr. 3, 1998.
Chern J-W, et al., Zhonghua Yaoxue Zazhi, Chinese Pharmaceutical Journal, vol. 48, No. 1, pp. 37-52 (1996), XP002962574.

*Primary Examiner* — Susanna Moore
(74) *Attorney, Agent, or Firm* — George W. Johnston; Patricia S. Roth-Tramaloni; Kimberly J. Prior

(57) ABSTRACT

The present invention relates to compounds of formula (I)

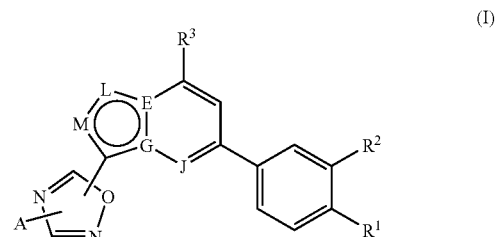

(I)

wherein A, E G, J, L, M, $R^1$, $R^2$, and $R^3$ are as defined in the specification and claims. The invention also relates to pharmaceutical compositions containing such compounds and methods for preparing the compounds and compositions. The compounds are metabotropic glutamate receptor antagonists and are useful for the treatment of a variety of CNS disorders.

13 Claims, No Drawings

SUBSTITUTED PYRAZOLO [1,5-A] PYRIMIDINES AS METABOTROPIC GLUTAMATE ANTAGONISTS

PRIORITY TO RELATED APPLICATIONS

This application is a division of U.S. application Ser. No. 11/524,135, filed Sep. 20, 2006, now pending; which claims the benefit of European Application No. 05108910.0, filed Sep. 27, 2005. The entire contents of the above-identified applications are hereby incorporated by reference.

BACKGROUND OF THE INVENTION

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) form the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the group II can be used for the treatment or prevention of acute and/or chronic neurological disorders such as psychosis, schizophrenia, Alzheimer's disease, cognitive disorders and memory deficits.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are chronic and acute pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia, depressions, colon cancer, sleep disorders, disorders of circadian rhythms and glioma since mGluR2 antagonists have been found to reduce cell proliferation in human glioma cells (J. Neurochem. March 2003, 84(6): 1288-95).

SUMMARY OF THE INVENTION

The present invention provides compounds of formula (I), pharmaceutical compositions containing them, processes for their manufacture and methods for treating CNS disorders with them.

In particular, the present invention provides compounds of formula (I)

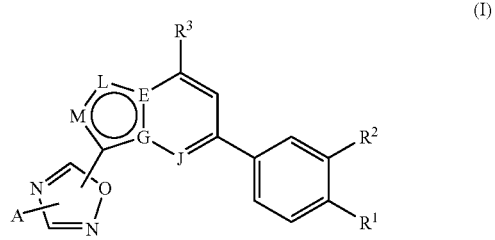

wherein
either E and J are N, G is C and one of L or M is N and the other is CH;
or L and G are N, E is C, and J and M are CH;
$R^1$ and $R^2$ are each independently H, halogen, $C_{1-6}$-alkyl optionally substituted by one or more F or by $C_{1-6}$-alkoxy, $C_{1-6}$-alkoxy optionally substituted by one or more F;
$R^3$ is H, —C(CH$_3$)$_2$OH, linear $C_{1-4}$-alkyl or $C_{3-4}$-cycloalkyl each of which is optionally substituted by one or more substituent(s) selected from the group consisting of 1 to 6 F and 1 to 2 OH;
A is selected from the group consisting of aryl and 5 or 6-membered heteroaryl optionally substituted by one to four $R^a$;
$R^a$ is F, OH, amino, $C_{1-6}$-alkyl optionally substituted by OH, $C_{1-6}$-alkoxy, $C_{3-4}$-cycloalkyl, —CO—$R^b$, SO$_2$R$^c$ or SO$_2$—NR$^d$R$^e$;
$R^b$ is amino;
$R^c$ is OH or $C_{1-6}$-alkyl;
$R^d$ and $R^e$ are the same or different and are selected from the group consisting of: H;
  straight or branched $C_{1-6}$-alkyl optionally substituted by one or more substituent(s) selected from the group consisting of F, cyano, OH, di(C$_{1-6}$-alkyl)amino, $C_{3-6}$-cycloalkyl, 5 or 6-membered heterocycloalkyl, aryl and 5 or 6-membered heteroaryl;
  $C_{3-6}$-cycloalkyl;
  aryl; and
  5 or 6-membered heteroaryl;
or $R^d$ and $R^e$, together with the nitrogen atom to which they are attached, form an heterocyclic ring of 4 to 6 ring members which is optionally substituted by OH or $C_{1-6}$-alkyl;
and pharmaceutically acceptable salts thereof.

The compounds of formula (I) can also be used in the form of their prodrugs. Examples are esters, N-oxides, phosphate esters, glycoamide esters, glyceride conjugates and the like. The prodrugs can add to the value of the present compounds advantages in absorption, pharmacokinetics in distribution and transport to the brain.

Compounds of formula I are metabotropic glutamate receptor antagonists. Compounds of formula I are distinguished by valuable therapeutic properties and are useful for the treatment of mGluR-mediated diseases, such as those mentioned above.

DETAILED DESCRIPTION OF THE INVENTION

Unless otherwise stated, the following terms used in the present description have the definitions given in the following. It must be noted that, as used in the specification and the appended claims, the singular forms "a", "an," and "the" include plural forms unless the context clearly dictates otherwise.

The term "alkyl" denotes straight-chain or branched saturated hydrocarbon residues with 1 to 6 carbon atoms ($C_{1-6}$-alkyl), preferably with 1 to 4 carbon atoms ($C_{1-4}$-alkyl), such as methyl, ethyl, n-propyl, i-propyl, i-butyl, t-butyl, as well as those groups which are illustrated with the exemplified compounds of the invention hereinafter.

The term "alkoxy" denotes an alkyl residue as defined above bound via an oxygen atom. Examples of "$C_{1-6}$-alkoxy" residues include methoxy, ethoxy, isopropoxy, as well as those groups which are illustrated with the exemplified compounds of the invention hereinafter. Examples of lower alkoxy substituted by one or more halogen include 2,2,2-trifluoroethoxy groups.

The term "amino" denotes an —$NH_2$ group.

The term "di($C_{1-6}$)alkylamino" denotes an —$NR^7R^8$ group, wherein $R^7$ and $R^8$ are independently $C_1$-$C_7$ alkyl groups as defined herein above. Examples of di($C_{1-6}$)alkylamino groups include but are not limited to di(methyl)amino, di(ethyl)amino, methylethylamino, as well as those groups which are illustrated with the exemplified compounds of the invention hereinafter.

The term "aryl" represents an aromatic carbocyclic group consisting of one individual ring, or one or more fused rings in which at least one ring is aromatic in nature. Preferred aryl groups are phenyl or naphthyl.

The term "heteroaryl or 5 or 6-membered heteroaryl" refers to an aromatic group having 5 to 6 ring atoms and containing one or more heteroatoms selected from nitrogen, oxygen and sulphur. Preferred are those heteroaryl groups wherein the heteroatom is selected from nitrogen. Examples of such heteroaryl groups include pyridinyl, pyrazinyl, pyrimidinyl or pyridazinyl, and in particular, pyridin-2-yl, pyridin-3-yl, pyridine-4-yl, pyrimidin-5-yl, thiazol-2-yl and thiophen-2-yl as well as those groups which are illustrated with the exemplified compounds of the invention hereinafter.

The term "halogen" embraces fluorine (F), chlorine (Cl), bromine (Br) and iodine (I).

The term "cycloalkyl" means a cycloalkyl group containing 3 to 12, preferably 3 to 8 carbon atoms, and still more preferably 3 to 6 carbon atoms, such as cyclopropyl, cyclobutyl, cyclopentyl or cyclohexyl. Cycloalkyl containing 3 to 4 carbon atoms are the most preferred.

The term "5 or 6-membered heterocycloalkyl" denotes a heterocyclic ring having 5 or 6 ring members comprising at least two carbon atoms as ring members and 1, 2 or 3 additional heteroatom(s) ring members selected from N, O and S, the remaining ring members being carbon atoms. Examples of 5 or 6 heterocycloalkyl rings include but are not limited to 1H-tetrazole; 2H-tetrazole; 1,2,3- and 1,24-triazole; imidazole; pyrrole; 1,2,3-, 1,3,4- or 1,2,5-thiadiazine; 1,4-oxazine; 1,2- or 1,4-thiazine; 4-morpholinyl; 1-pyrrolidinyl; 1-piperazinyl, preferably 4-morpholinyl; 1-pyrrolidinyl or 1-piperazinyl as well as those groups which are illustrated with the exemplified compounds of the invention hereinafter. Substituents for such 5 or 6 membered heterocyclic ring include but are not limited to halo, amino, nitro, cyano, OH, $C_{1-6}$-alkyl optionally substituted by OH, $C_{1-6}$-alkoxy, $C_{2-6}$-alkenyl, $C_{3-8}$-cycloalkyl, or $CF_3$, and preferably $C_{1-6}$-alkyl or $CF_3$ as well as those groups which are illustrated with the exemplified compounds of the invention hereinafter.

The term "heterocyclic ring of 4 to 6 ring members" denotes a 4 to 6 membered ring containing one or two heteroatoms selected from N, O, and S, the remaining ring members being carbon atoms.

The term "$C_{2-6}$-alkenyl" denotes a straight- or branched-carbon chain group containing from 2 to 7 carbon atoms and containing 1, 2 or 3 double bond(s), preferably 1 to 4 carbon atoms and 1 double bond. Examples of such groups are methenyl, 1-ethenyl, 2-ethenyl, 1-propenyl, 2-propenyl, 3-propenyl, isopropenyl, isobutenyl, sec-butenyl, tert-butenyl, pentenyl, and n-hexenyl as well as those specifically illustrated by the examples herein below.

The term "thiophenyl" as used herein is synonymous with "thienyl" and denotes a thiophene substituent, i.e., $C_4H_4S$.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable addition salt" refers to any salt derived from an inorganic or organic acid or base.

"Therapeutically effective amount" means an amount that is effective to prevent, alleviate or ameliorate symptoms of disease or prolong the survival of the subject being treated.

In particular, the present invention provides compounds of formula (I)

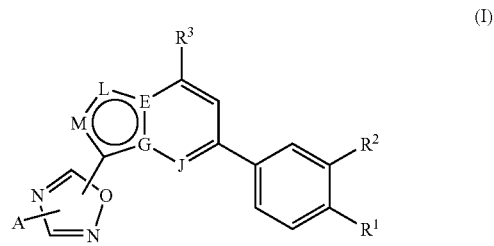

(I)

wherein either E and J are N, G is C and one of L or M is N and the other is CH;

or L and G are N, E is C, and J and M are CH;

$R^1$ and $R^2$ are each independently H, halogen, $C_{1-6}$-alkyl optionally substituted by one or more F or by $C_{1-6}$-alkoxy, $C_{1-6}$-alkoxy optionally substituted by one or more F;

$R^3$ is H, —$C(CH_3)_2OH$, linear $C_{1-4}$-alkyl or $C_{3-4}$-cycloalkyl each of which is optionally substituted by one or more substituent(s) selected from the group consisting of 1 to 6 F and 1 to 2 OH;

A is selected from the group consisting of aryl and 5 or 6-membered heteroaryl optionally substituted by one to four $R^a$;

$R^a$ is F, OH, amino, $C_{1-6}$-alkyl optionally substituted by OH, $C_{1-6}$-alkoxy, $C_{3-4}$-cycloalkyl, —CO—$R^b$ $SO_2R^c$ or $SO_2$—$NR^dR^e$;

$R^b$ is amino;

$R^c$ is OH or $C_{1-6}$-alkyl;

$R^d$ and $R^e$ are the same or different and are selected from the group consisting of: H;

straight or branched $C_{1-6}$-alkyl optionally substituted by one or more substituent(s) selected from the group consisting of F, cyano, OH, di($C_{1-6}$-alkyl)amino, $C_{3-6}$-cycloalkyl, 5 or 6-membered heterocycloalkyl, aryl and 5 or 6-membered heteroaryl;

$C_{3-6}$-cycloalkyl;

aryl; and 5 or 6-membered heteroaryl;

or $R^d$ and $R^e$, together with the nitrogen atom to which they are attached, form an heterocyclic ring of 4 to 6 ring members which is optionally substituted by OH or $C_{1-6}$-alkyl;

and pharmaceutically acceptable salts thereof.

Also encompassed by the compounds of formula (I) according to the invention are those compounds of formula (I-a):

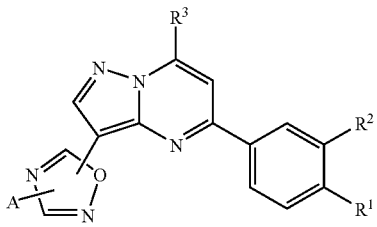

(I-a)

wherein A and $R^1$ to $R^3$ are as defined hereinabove in connection with formula (I).

In a certain embodiment the compounds of the invention are those compounds of formula (I-a), wherein:
$R^1$ is halo or $CF_3$;
$R^2$ is H, halo, or $C_{1-6}$-alkyl or $C_{1-6}$-alkoxy each of which is optionally substituted by one or more F;
$R^3$ is H, linear $C_{1-4}$-alkyl, preferably methyl, or $C_{3-4}$-cycloalkyl, preferably cyclopropyl, each of which is optionally substituted by 1 to 6 F, preferably by 2 or 3 F;
A is selected from the group consisting of aryl, preferably phenyl, and 5 or 6-membered heteroaryl, preferably thiophenyl, pyridinyl, pyrimidinyl or pyrazolyl, each of which is optionally substituted by one to four $R^a$;
$R^a$ is amino or $SO_2$—$NR^dR^e$; wherein $R^d$ and $R^e$ are each H; and pharmaceutically acceptable salts thereof.

Preferred compounds of formula (I-a) are those compounds of formula (I-a), wherein:
$R^1$ is Cl, F or $CF_3$;
$R^2$ is H, F, Cl, methyl, OEt, $CHF_2$, $CF_3$, $OCF_3$ or $OCH_2CF_3$;
$R^3$ is H, methyl or cyclopropyl, wherein the methyl and cyclopropyl group are each optionally substituted by 2 or 3 F;
A is selected from the group consisting of phenyl, thiophenyl, pyridinyl, pyrimidinyl and pyrazolyl, each of which is optionally substituted by one $R^a$;
$R^a$ is amino or $SO_2$—$NR^dR^e$; wherein $R^d$ and $R^e$ are each H; and pharmaceutically acceptable salts thereof, for example the following compounds:
4-{5-[7-Trifluoromethyl-5-(4-trifluoromethyl-phenyl)-pyrazolo[1,5-a]pyrimidin-3-yl]-[1,2,4]oxadiazol-3-yl}-benzenesulfonamide;
3-{5-[7-Trifluoromethyl-5-(4-trifluoromethyl-phenyl)-pyrazolo[1,5-a]pyrimidin-3-yl]-[1,2,4]oxadiazol-3-yl}-benzenesulfonamide;
3-(3-Pyridin-3-yl-[1,2,4]oxadiazol-5-yl)-7-trifluoromethyl-5-(4-trifluoromethyl-phenyl)-pyrazolo[1,5-a]pyrimidine;
4-{5-[7-Difluoromethyl-5-(4-trifluoromethyl-phenyl)-pyrazolo[1,5-a]pyrimidin-3-yl]-[1,2,4]oxadiazol-3-yl}-benzenesulfonamide;
3-{5-[7-Difluoromethyl-5-(4-trifluoromethyl-phenyl)-pyrazolo[1,5-a]pyrimidin-3-yl]-[1,2,4]oxadiazol-3-yl}-benzenesulfonamide;
3-{5-[5-(4-Chloro-phenyl)-7-cyclopropyl-pyrazolo[1,5-a]pyrimidin-3-yl]-[1,2,4]oxadiazol-3-yl}-benzenesulfonamide;
3-{5-[7-Cyclopropyl-5-(4-trifluoromethyl-phenyl)-pyrazolo[1,5-a]pyrimidin-3-yl]-[1,2,4]oxadiazol-3-yl}-benzenesulfonamide;
4-{5-[5-(4-Chloro-phenyl)-7-cyclopropyl-pyrazolo[1,5-a]pyrimidin-3-yl]-[1,2,4]oxadiazol-3-yl}-benzenesulfonamide;
4-{5-[7-Cyclopropyl-5-(4-trifluoromethyl-phenyl)-pyrazolo[1,5-a]pyrimidin-3-yl]-[1,2,4]oxadiazol-3-yl}-benzenesulfonamide;
3-{5-[5-(4-Chloro-phenyl)-7-trifluoromethyl-pyrazolo[1,5-a]pyrimidin-3-yl]-[1,2,4]oxadiazol-3-yl}-benzenesulfonamide;
4-{5-[5-(4-Chloro-phenyl)-7-trifluoromethyl-pyrazolo[1,5-a]pyrimidin-3-yl]-[1,2,4]oxadiazol-3-yl}-benzenesulfonamide;
4-{3-[7-Trifluoromethyl-5-(4-trifluoromethyl-phenyl)-pyrazolo[1,5-a]pyrimidin-3-yl]-[1,2,4]oxadiazol-5-yl}-benzenesulfonamide;
3-{3-[7-Trifluoromethyl-5-(4-trifluoromethyl-phenyl)-pyrazolo[1,5-a]pyrimidin-3-yl]-[1,2,4]oxadiazol-5-yl}-benzenesulfonamide;
3-(5-{5-[3-(2,2,2-Trifluoro-ethoxy)-4-trifluoromethyl-phenyl]-7-trifluoromethyl-pyrazolo[1,5-a]pyrimidin-3-yl}-[1,2,4]oxadiazol-3-yl)-benzenesulfonamide;
3-{5-[5-(3-Methyl-4-trifluoromethyl-phenyl)-7-trifluoromethyl-pyrazolo[1,5-a]pyrimidin-3-yl]-[1,2,4]oxadiazol-3-yl}-benzenesulfonamide;
4-{5-[5-(3-Methyl-4-trifluoromethyl-phenyl)-7-trifluoromethyl-pyrazolo[1,5-a]pyrimidin-3-yl]-[1,2,4]oxadiazol-3-yl}-benzenesulfonamide;
3-{5-[5-(4-Chloro-phenyl)-7-difluoromethyl-pyrazolo[1,5-a]pyrimidin-3-yl]-[1,2,4]oxadiazol-3-yl}-benzenesulfonamide;
5-{5-[5-(4-Chloro-phenyl)-7-cyclopropyl-pyrazolo[1,5-a]pyrimidin-3-yl]-[1,2,4]oxadiazol-3-yl}-thiophene-2-sulfonic acid amide;
5-{5-[5-(3-Methyl-4-trifluoromethyl-phenyl)-7-trifluoromethyl-pyrazolo[1,5-a]pyrimidin-3-yl]-[1,2,4]oxadiazol-3-yl}-thiophene-2-sulfonic acid amide;
5-(5-{5-[3-(2,2,2-Trifluoro-ethoxy)-4-trifluoromethyl-phenyl]-7-trifluoromethyl-pyrazolo[1,5-a]pyrimidin-3-yl}-[1,2,4]oxadiazol-3-yl)-thiophene-2-sulfonic acid amide;
5-{5-[7-Cyclopropyl-5-(4-trifluoromethyl-phenyl)-pyrazolo[1,5-a]pyrimidin-3-yl]-[1,2,4]oxadiazol-3-yl}-thiophene-2-sulfonic acid amide;
4-{5-[7-Trifluoromethyl-5-(3-trifluoromethyl-phenyl)-pyrazolo[1,5-a]pyrimidin-3-yl]-[1,2,4]oxadiazol-3-yl}-benzenesulfonamide;
3-{5-[7-Trifluoromethyl-5-(3-trifluoromethyl-phenyl)-pyrazolo[1,5-a]pyrimidin-3-yl]-[1,2,4]oxadiazol-3-yl}-benzenesulfonamide;
5-{5-[7-Trifluoromethyl-5-(4-trifluoromethyl-phenyl)-pyrazolo[1,5-a]pyrimidin-3-yl]-[1,2,4]oxadiazol-3-yl}-thiophene-2-sulfonic acid amide;
5-{5-[5-(4-Chloro-phenyl)-7-trifluoromethyl-pyrazolo[1,5-a]pyrimidin-3-yl]-[1,2,4]oxadiazol-3-yl}-thiophene-2-sulfonic acid amide;
5-{5-[5-(4-Chloro-phenyl)-7-difluoromethyl-pyrazolo[1,5-a]pyrimidin-3-yl]-[1,2,4]oxadiazol-3-yl}-thiophene-2-sulfonic acid amide;
5-{5-[7-Methyl-5-(4-trifluoromethyl-phenyl)-pyrazolo[1,5-a]pyrimidin-3-yl]-[1,2,4]oxadiazol-3-yl}-thiophene-2-sulfonic acid amide;
5-{5-[7-Difluoromethyl-5-(4-trifluoromethyl-phenyl)-pyrazolo[1,5-a]pyrimidin-3-yl]-[1,2,4]oxadiazol-3-yl}-thiophene-2-sulfonic acid amide;
5-{5-[5-(4-Chloro-phenyl)-7-methyl-pyrazolo[1,5-a]pyrimidin-3-yl]-[1,2,4]oxadiazol-3-yl}-thiophene-2-sulfonic acid amide;
5-{3-[7-Trifluoromethyl-5-(4-trifluoromethyl-phenyl)-pyrazolo[1,5-a]pyrimidin-3-yl]-[1,2,4]oxadiazol-5-yl}-thiophene-2-sulfonic acid amide;

5-{5-[7-Trifluoromethyl-5-(3-trifluoromethyl-phenyl)-pyrazolo[1,5-a]pyrimidin-3-yl]-[1,2,4]oxadiazol-3-yl}-pyridin-2-ylamine;
5-{5-[7-Trifluoromethyl-5-(4-trifluoromethyl-phenyl)-pyrazolo[1,5-a]pyrimidin-3-yl]-[1,2,4]oxadiazol-3-yl}-pyridin-2-ylamine;
5-{5-[7-Difluoromethyl-5-(4-trifluoromethyl-phenyl)-pyrazolo[1,5-a]pyrimidin-3-yl]-[1,2,4]oxadiazol-3-yl}-pyridin-2-ylamine;
5-{5-[5-(3-Methyl-4-trifluoromethyl-phenyl)-7-trifluoromethyl-pyrazolo[1,5-a]pyrimidin-3-yl]-[1,2,4]oxadiazol-3-yl}-pyridin-2-ylamine;
3-{5-[5-(4-Chloro-phenyl)-7-methyl-pyrazolo[1,5-a]pyrimidin-3-yl]-[1,2,4]oxadiazol-3-yl}-benzenesulfonamide;
5-{5-[7-Trifluoromethyl-5-(4-trifluoromethyl-phenyl)-pyrazolo[1,5-a]pyrimidin-3-yl]-[1,2,4]oxadiazol-3-yl}-pyrimidin-2-ylamine;
3-{5-[5-(4-Chloro-phenyl)-pyrazolo[1,5-a]pyrimidin-3-yl]-[1,2,4]oxadiazol-3-yl}-benzenesulfonamide;
5-{5-[5-(4-Trifluoromethyl-phenyl)-pyrazolo[1,5-a]pyrimidin-3-yl]-[1,2,4]oxadiazol-3-yl}-thiophene-2-sulfonic acid amide;
3-{5-[5-(4-Trifluoromethyl-phenyl)-pyrazolo[1,5-a]pyrimidin-3-yl]-[1,2,4]oxadiazol-3-yl}-benzenesulfonamide;
4-{5-[7-Trifluoromethyl-5-(4-trifluoromethyl-phenyl)-pyrazolo[1,5-a]pyrimidin-3-yl]-[1,2,4]oxadiazol-3-yl}-pyridin-2-ylamine;
4-{5-[5-(4-Trifluoromethyl-phenyl)-pyrazolo[1,5-a]pyrimidin-3-yl]-[1,2,4]oxadiazol-3-yl}-pyridin-2-ylamine;
5-{5-[5-(4-Chloro-phenyl)-7-trifluoromethyl-pyrazolo[1,5-a]pyrimidin-3-yl]-[1,2,4]oxadiazol-3-yl}-pyridin-2-ylamine;
5-{5-[5-(4-Chloro-phenyl)-7-difluoromethyl-pyrazolo[1,5-a]pyrimidin-3-yl]-[1,2,4]oxadiazol-3-yl}-pyridin-2-ylamine;
5-{5-[5-(4-Chloro-3-methyl-phenyl)-7-trifluoromethyl-pyrazolo[1,5-a]pyrimidin-3-yl]-[1,2,4]oxadiazol-3-yl}-pyridin-2-ylamine;
5-{5-[7-Difluoromethyl-5-(3-methyl-4-trifluoromethyl-phenyl)-pyrazolo[1,5-a]pyrimidin-3-yl]-[1,2,4]oxadiazol-3-yl}-pyridin-2-ylamine;
5-{5-[5-(3,4-Dichloro-phenyl)-7-difluoromethyl-pyrazolo[1,5-a]pyrimidin-3-yl]-[1,2,4]oxadiazol-3-yl}-pyridin-2-ylamine;
5-{5-[5-(3,4-Dichloro-phenyl)-7-trifluoromethyl-pyrazolo[1,5-a]pyrimidin-3-yl]-[1,2,4]oxadiazol-3-yl}-pyridin-2-ylamine;
5-{5-[7-Difluoromethyl-5-(3-ethoxy-4-trifluoromethyl-phenyl)-pyrazolo[1,5-a]pyrimidin-3-yl]-[1,2,4]oxadiazol-3-yl}-pyridin-2-ylamine;
5-{5-[5-(3-Ethoxy-4-trifluoromethyl-phenyl)-7-trifluoromethyl-pyrazolo[1,5-a]pyrimidin-3-yl]-[1,2,4]oxadiazol-3-yl}-pyridin-2-ylamine;
5-(5-{5-[3-(2,2,2-Trifluoro-ethoxy)-4-trifluoromethyl-phenyl]-7-trifluoromethyl-pyrazolo[1,5-a]pyrimidin-3-yl}-[1,2,4]oxadiazol-3-yl)-pyridin-2-ylamine;
5-(5-{7-Difluoromethyl-5-[3-(2,2,2-trifluoro-ethoxy)-4-trifluoromethyl-phenyl]-pyrazolo[1,5-a]pyrimidin-3-yl}-[1,2,4]oxadiazol-3-yl)-pyridin-2-ylamine;
5-{5-[5-(3-Chloro-4-trifluoromethyl-phenyl)-7-difluoromethyl-pyrazolo[1,5-a]pyrimidin-3-yl]-[1,2,4]oxadiazol-3-yl}-pyridin-2-ylamine;
5-{5-[5-(3-Chloro-4-trifluoromethyl-phenyl)-7-trifluoromethyl-pyrazolo[1,5-a]pyrimidin-3-yl]-[1,2,4]oxadiazol-3-yl}-pyridin-2-ylamine;
5-{5-[7-Difluoromethyl-5-(3-fluoro-4-trifluoromethyl-phenyl)-pyrazolo[1,5-a]pyrimidin-3-yl]-[1,2,4]oxadiazol-3-yl}-pyridin-2-ylamine;
5-{5-[5-(3-Fluoro-4-trifluoromethyl-phenyl)-7-trifluoromethyl-pyrazolo[1,5-a]pyrimidin-3-yl]-[1,2,4]oxadiazol-3-yl}-pyridin-2-ylamine;
5-{5-[5-(3,4-Difluoro-phenyl)-7-trifluoromethyl-pyrazolo[1,5-a]pyrimidin-3-yl]-[1,2,4]oxadiazol-3-yl}-pyridin-2-ylamine;
5-{5-[5-(4-Chloro-3-methyl-phenyl)-7-difluoromethyl-pyrazolo[1,5-a]pyrimidin-3-yl]-[1,2,4]oxadiazol-3-yl}-pyridin-2-ylamine;
5-{5-[5-(3,4-Difluoro-phenyl)-7-trifluoromethyl-pyrazolo[1,5-a]pyrimidin-3-yl]-[1,2,4]oxadiazol-3-yl}-pyrimidin-2-ylamine;
5-{5-[5-(3-Fluoro-4-trifluoromethyl-phenyl)-7-trifluoromethyl-pyrazolo[1,5-a]pyrimidin-3-yl]-[1,2,4]oxadiazol-3-yl}-pyrimidin-2-ylamine;
5-{5-[5-(3-Chloro-4-trifluoromethyl-phenyl)-7-trifluoromethyl-pyrazolo[1,5-a]pyrimidin-3-yl]-[1,2,4]oxadiazol-3-yl}-pyrimidin-2-ylamine;
5-{5-[5-(3,4-Dichloro-phenyl)-7-trifluoromethyl-pyrazolo[1,5-a]pyrimidin-3-yl]-[1,2,4]oxadiazol-3-yl}-pyrimidin-2-ylamine;
5-{5-[5-(4-Chloro-phenyl)-7-trifluoromethyl-pyrazolo[1,5-a]pyrimidin-3-yl]-[1,2,4]oxadiazol-3-yl}-pyrimidin-2-ylamine;
5-{5-[5-(3-Methyl-4-trifluoromethyl-phenyl)-7-trifluoromethyl-pyrazolo[1,5-a]pyrimidin-3-yl]-[1,2,4]oxadiazol-3-yl}-pyrimidin-2-ylamine;
5-{5-[5-(4-Chloro-3-methyl-phenyl)-7-trifluoromethyl-pyrazolo[1,5-a]pyrimidin-3-yl]-[1,2,4]oxadiazol-3-yl}-pyrimidin-2-ylamine;
4-{5-[5-(4-Chloro-phenyl)-7-trifluoromethyl-pyrazolo[1,5-a]pyrimidin-3-yl]-[1,2,4]oxadiazol-3-yl}-pyridin-2-ylamine;
4-{5-[5-(3,4-Dichloro-phenyl)-7-trifluoromethyl-pyrazolo[1,5-a]pyrimidin-3-yl]-[1,2,4]oxadiazol-3-yl}-pyridin-2-ylamine; and
4-{5-[5-(3-Methyl-4-trifluoromethyl-phenyl)-7-trifluoromethyl-pyrazolo[1,5-a]pyrimidin-3-yl]-[1,2,4]oxadiazol-3-yl}-pyridine-2-ylamine.

Also encompassed by the compounds of formula (I) according to the invention are those compounds of formula (I-b):

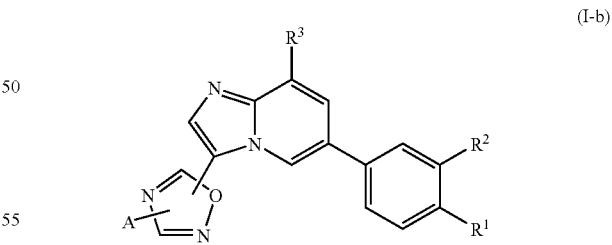

wherein A and $R^1$ to $R^3$ are as defined hereinabove in connection with formula (I).

In a certain embodiment the compounds of the invention are those compounds of formula (I-b), wherein:
$R^1$ is halo or $CF_3$;
$R^2$ is H, halo, or $C_{1-6}$-alkyl or $C_{1-6}$-alkoxy each of which is optionally substituted by one or more F;
$R^3$ is H, linear $C_{1-4}$-alkyl, preferably methyl, or $C_{3-4}$-cycloalkyl, preferably cyclopropyl, each of which is optionally substituted by 1 to 6 F, preferably by 2 or 3 F;

A is selected from the group consisting of aryl, preferably phenyl, and 5 or 6-membered heteroaryl, preferably thiophenyl, pyridinyl, pyrimidinyl or pyrazolyl, each of which is optionally substituted by one to four $R^a$;

$R^a$ is amino or $SO_2-NR^dR^e$; wherein $R^d$ and $R^e$ are each H;

and pharmaceutically acceptable salts thereof.

Preferred compounds of formula (I-b) are those compounds of formula (I-b), wherein:

$R^1$ is Cl, F or $CF_3$;

$R^2$ is H, F, Cl, methyl, OEt, $CHF_2$, $CF_3$, $OCF_3$ or $OCH_2CF_3$;

$R^3$ is H, methyl or cyclopropyl, each of which is optionally substituted by 2 or 3 F;

A is selected from the group consisting of phenyl, thiophenyl, pyridinyl, pyrimidinyl and pyrazolyl, each of which is optionally substituted by one $R^a$;

$R^a$ is amino or $SO_2-NR^dR^e$; wherein $R^d$ and $R^e$ are each H;

and pharmaceutically acceptable salts thereof, for example the following compounds:

3-{5-[8-Trifluoromethyl-6-(4-trifluoromethyl-phenyl)-imidazo[1,2-a]pyridin-3-yl]-[1,2,4]oxadiazol-3-yl}-benzenesulfonamide;

4-{5-[8-Trifluoromethyl-6-(4-trifluoromethyl-phenyl)-imidazo[1,2-a]pyridin-3-yl]-[1,2,4]oxadiazol-3-yl}-benzenesulfonamide;

4-{5-[6-(4-Chloro-phenyl)-8-methyl-imidazo[1,2-a]pyridin-3-yl]-[1,2,4]oxadiazol-3-yl}-benzenesulfonamide;

3-{5-[6-(4-Chloro-phenyl)-8-methyl-imidazo[1,2-a]pyridin-3-yl]-[1,2,4]oxadiazol-3-yl}-benzenesulfonamide;

5-{5-[6-(4-Chloro-phenyl)-8-methyl-imidazo[1,2-a]pyridin-3-yl]-[1,2,4]oxadiazol-3-yl}-thiophene-2-sulfonic acid amide;

4-{5-[8-Methyl-6-(4-trifluoromethyl-phenyl)-imidazo[1,2-a]pyridin-3-yl]-[1,2,4]oxadiazol-3-yl}-benzenesulfonamide;

3-{5-[8-Methyl-6-(4-trifluoromethyl-phenyl)-imidazo[1,2-a]pyridin-3-yl]-[1,2,4]oxadiazol-3-yl}-benzenesulfonamide;

5-{5-[8-Methyl-6-(4-trifluoromethyl-phenyl)-imidazo[1,2-a]pyridin-3-yl]-[1,2,4]oxadiazol-3-yl}-thiophene-2-sulfonic acid amide;

5-{5-[8-Methyl-6-(4-trifluoromethyl-phenyl)-imidazo[1,2-a]pyridin-3-yl]-[1,2,4]oxadiazol-3-yl}-pyridin-2-ylamine;

5-{5-[8-Methyl-6-(4-trifluoromethyl-phenyl)-imidazo[1,2-a]pyridin-3-yl]-[1,2,4]oxadiazol-3-yl}-pyrimidin-2-ylamine;

4-{5-[6-(4-Trifluoromethyl-phenyl)-imidazo[1,2-a]pyridin-3-yl]-[1,2,4]oxadiazol-3-yl}-benzenesulfonamide;

3-{5-[6-(4-Trifluoromethyl-phenyl)-imidazo[1,2-a]pyridin-3-yl]-[1,2,4]oxadiazol-3-yl}-benzenesulfonamide;

5-{5-[6-(4-Trifluoromethyl-phenyl)-imidazo[1,2-a]pyridin-3-yl]-[1,2,4]oxadiazol-3-yl}-thiophene-2-sulfonic acid amide;

5-{5-[6-(4-Chloro-phenyl)-imidazo[1,2-a]pyridin-3-yl]-[1,2,4]oxadiazol-3-yl}-thiophene-2-sulfonic acid amide;

5-{5-[6-(4-Trifluoromethyl-phenyl)-imidazo[1,2-a]pyridin-3-yl]-[1,2,4]oxadiazol-3-yl}-pyridin-2-ylamine;

5-{5-[6-(4-Chloro-phenyl)-imidazo[1,2-a]pyridin-3-yl]-[1,2,4]oxadiazol-3-yl}-pyridin-2-ylamine;

4-{5-[8-Methyl-6-(4-trifluoromethyl-phenyl)-imidazo[1,2-a]pyridin-3-yl]-[1,2,4]oxadiazol-3-yl}-pyridin-2-ylamine; and 4-{5-[6-(4-Trifluoromethyl-phenyl)-imidazo[1,2-a]pyridin-3-yl]-[1,2,4]oxadiazol-3-yl}-pyridin-2-ylamine.

Also encompassed by the compounds of formula (I) according to the invention are those compounds of formula (I-c):

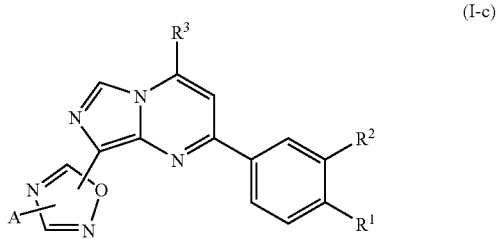

(I-c)

wherein A and $R^1$ to $R^3$ are as defined hereinabove in connection with formula (I).

In a certain embodiment the compounds of the invention are those compounds of formula (I-c), wherein:

$R^1$ is halo or $CF_3$;

$R^2$ is H, halo, or $C_{1-6}$-alkyl or $C_{1-6}$-alkoxy each of which is optionally substituted by one or more F;

$R^3$ is H, linear $C_{1-4}$-alkyl, preferably methyl, or $C_{3-4}$-cycloalkyl, preferably cyclopropyl, each of which is optionally substituted by 1 to 6 F, preferably by 2 or 3 F;

A is selected from the group consisting of aryl, preferably phenyl, and 5 or 6-membered heteroaryl, preferably thiophenyl, pyridinyl, pyrimidinyl or pyrazolyl, each of which is optionally substituted by one to four $R^a$;

$R^a$ is amino or $SO_2-NR^dR^e$; wherein $R^d$ and $R^e$ are each H;

and pharmaceutically acceptable salts thereof.

Preferred compounds of formula (I-c) are those compounds of formula (I-c), wherein:

$R^1$ is Cl, F or $CF_3$;

$R^2$ is H, F, Cl, methyl, OEt, $CHF_2$, $CF_3$, $OCF_3$ or $OCH_2CF_3$;

$R^3$ is H, methyl or cyclopropyl, each of which is optionally substituted by 2 or 3 F;

A is selected from the group consisting of phenyl, thiophenyl, pyridinyl, pyrimidinyl and pyrazolyl, each of which is optionally substituted by one $R^a$;

$R^a$ is amino or $SO_2-NR^dR^e$; wherein $R^d$ and $R^e$ are each H;

and pharmaceutically acceptable salts thereof, for example the following compounds:

4-{3-[4-Trifluoromethyl-2-(4-trifluoromethyl-phenyl)-imidazo[1,5-a]pyrimidin-8-yl]-[1,2,4]oxadiazol-5-yl}-benzenesulfonamide; and 5-{5-[4-Trifluoromethyl-2-(4-trifluoromethyl-phenyl)-imidazo[1,5-a]pyrimidin-8-yl]-[1,2,4]oxadiazol-3-yl}-thiophene-2-sulfonic acid amide.

The pharmaceutically acceptable addition salts of the compounds of the invention can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid, citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formulae (I), (I-a), (I-b) and (I-c).

The invention also encompasses a process for the preparation of the compounds of formula (I) according to the invention, said process comprising:

a) reacting a compound of formula (VI):

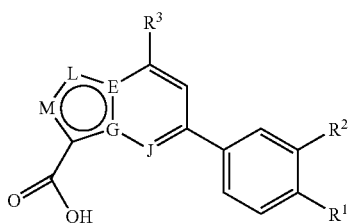

(VI)

with a compound of formula (VIII):

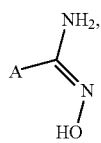

(VIII)

or b) reacting a compound of formula (IX):

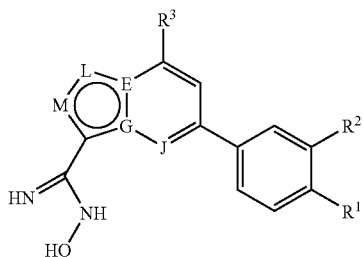

(IX)

with a compound of formulae (X)

(X)

to obtain a compound of formula (I), wherein $R^1$ to $R^3$ and A are as defined hereinabove in connection with formula (I).

The synthesis of the intermediate compounds of formula (VI) above can be carried out in accordance with the following general procedure I, which procedure is outlined below in scheme 1. As for the reaction of the compound of formula (VIII) with the compound of formula (VI), it can be for example carried out in accordance with the following general procedure II which procedure is outlined below in scheme 2. In these schemes, $R^1$, $R^2$, $R^3$, $R^4$ and p are as defined hereinabove. Procedures I and II are applicable for the preparation of all the compounds according to formula (I). Unless otherwise specified, all the compounds described in general procedures and schemes I and II are commercially available.

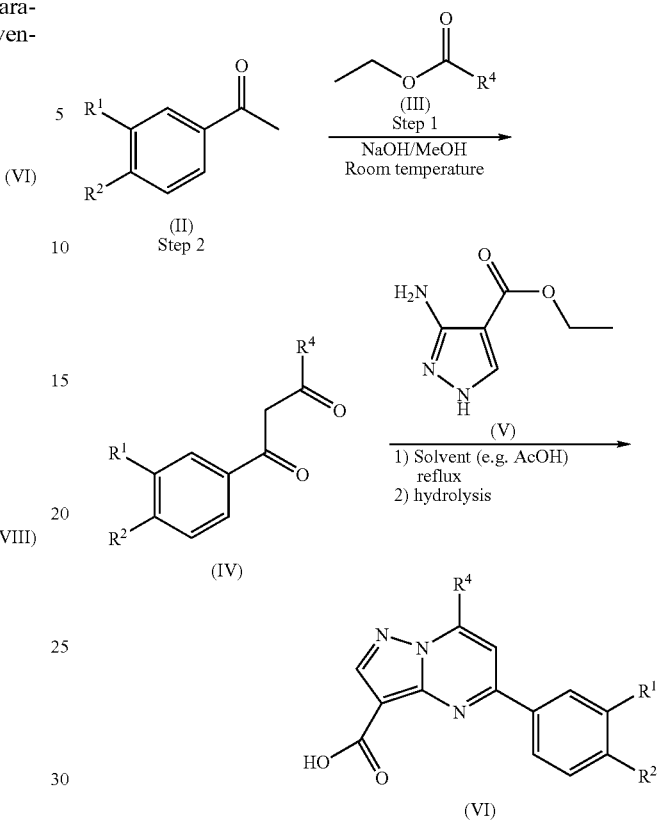

General Procedure I

Step 1:

To a stirred solution of commercially available compound of formula (III) in an organic solvent (e.g. tert-butyl-methyl-ether) is added at room temperature a solution of sodium methanolate in methanol followed by a solution of compound of formula (II) in an organic solvent (e.g. tert-butyl-methyl-ether). The reaction mixture is stirred at room temperature for about 19 h, cooled, acidified and extracted (e.g. with diethyl ether). The combined organic layers are washed and dried (e.g. $MgSO_4$) and evaporated to give crude compound of formula (IV) which can be used without further purification. Compounds of formula (II) are either commercially available or prepared according to examples A.1 to A.6.

Step 2:

A stirred mixture of commercially available compound of formula (V) (e.g. 3-amino-4-ethoxycarbonyl-pyrazole) and compound of formula (IV) in an organic acid (e.g. acetic acid) is heated under reflux conditions for about 1.5 h. The reaction mixture is evaporated, and the crude product is dissolved in a mixture of a concentrated base (e.g. KOH in methanol and water). The reaction mixture is stirred at about 60° C. for about 1.5 h, cooled, acidified and concentrated. The precipitate is collected by filtration and further purified (e.g. by crystallization from diethylether/methanol) to give the compound of formula (VI).

Scheme 2

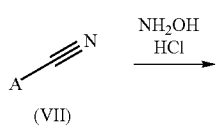

(VII)

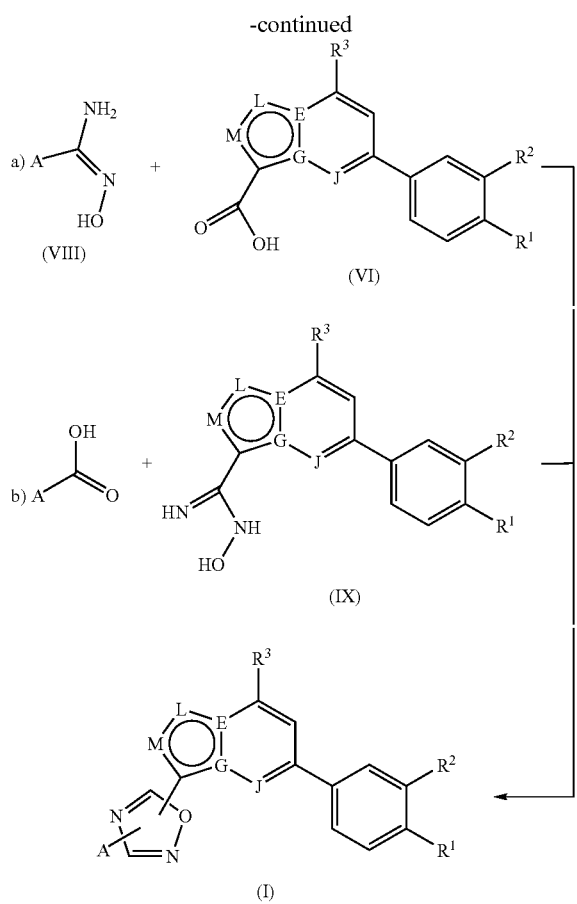

General Procedure II (Oxadiazoles)

The compounds of the invention of formula (I) can be obtained either with route a) or with route b).

In route a), to a stirred solution of a carboxylic acid (0.5 mmol) in DMF (5 ml) is added at room temperature a compound of formula (VII) (e.g. 1,1'-carbonyl-diimidazol (0.75 mmol)), and the reaction mixture is allowed to stir at room temperature for 2 h. The corresponding compound of formula (VIII) (e.g. N-hydroxy-amidine (0.75 mmol)) is added, the reaction mixture is stirred at 80° C. for 15 h and evaporated to dryness. Acetic acid (7.5 ml) is added, the stirred reaction mixture heated under reflux conditions for 4 h and evaporated. Purification by chromatography on silica gel and crystallization yielded the final product.

In route b) a commercially available carboxylic acid of formula (X) is added to a compound of formula (IX). The compounds of formula (IX) are prepared from the corresponding nitrites following the same method as described for the synthesis of compounds of formula (VIII) (see hereinafter: synthesis of intermediates compounds: N-hydroxy-amidines of formulae (VIII) and (IX) and examples B.1 to B.6).

The compounds of formula (I) and their pharmaceutically acceptable salts are metabotropic glutamate receptor antagonists and can be used for the treatment or prevention of acute and/or chronic neurological disorders, such as psychosis, schizophrenia, Alzheimer's disease, cognitive disorders and memory deficits. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are acute and chronic pain, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia, depression, colon cancer, sleep disorders, disorders of circadian rhythms and glioma.

The present invention also provides pharmaceutical compositions containing compounds of formula (I) or pharmaceutically acceptable salts thereof and a pharmaceutically acceptable carrier. Such pharmaceutical compositions can be in the form of tablets, coated tablets, dragees, hard and soft gelatin capsules, solutions, emulsions or suspensions. The pharmaceutical compositions also can be in the form of suppositories, or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

The compounds of the invention can be administered in a conventional manner, for example, orally, rectally, or parenterally. The compounds of the invention can be administered orally, for example, in the form of tablets, coated tablets, dragees, hard and soft gelatine capsules, solutions, emulsions, or suspensions. The compounds also can be administered rectally, for example, in the form of suppositories, or parenterally, for example, in the form of injection solutions.

The present invention relates also to methods for treating acute and/or chronic neurological disorders of the aforementioned kind by administering a therapeutically effective amount of a compound of the invention.

The dosage at which the compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The compounds of the present invention are group II mGlu receptor antagonists. The compounds show activities, as measured in the assay described below, of 0.150 µM or less, typically 0.030 µM or less, and ideally of 0.010 µM or less. In the table below are described some specific Ki values of some representative compounds.

|  | Ex. No. | | | | | |
| --- | --- | --- | --- | --- | --- | --- |
|  | 1 | 3 | 11 | 20 | 21 | 34 |
| $K_i$ mGlu2 (µM) | 0.0056 | 0.0481 | 0.0088 | 0.0161 | 0.0102 | 0.051 |

|  | Ex. No. | | | | | |
| --- | --- | --- | --- | --- | --- | --- |
|  | 41 | 42 | 46 | 47 | 48 | 77 |
| Ki mGlu2 (µM) | 0.0213 | 0.0146 | 0.0145 | 0.0077 | 0.0065 | 0.0255 |

[$^3$H]-LY354740 Binding on mGlu2 Transfected CHO Cell Membranes.
Transfection and Cell Culture cDNA encoding the rat mGlu2 receptor protein in pBluescript II was subcloned into the eukaryotic expression vector pcDNA I-amp from Invitrogen Ltd (Paisley, UK). This vector construct (pcDlmGR2) was co-transfected with a psvNeo plasmid encoding the gene for neomycin resistance, into CHO cells by a modified calcium phosphate method described by Chen & Okayama (1988). The cells were maintained in Dulbecco's Modified Eagle medium with reduced L-glutamine (2 mM final concentration) and 10% dialysed foetal calf serum from Gibco-Invitrogen (Carlsbad, Calif., USA). Selection was made in the presence of G-418 (1000 ug/ml final) and MCPG??. Clones were identified by reverse transcription of 5 µg total RNA, followed by PCR using mGlu2 receptor specific primers 5'-atcactgcttgggtttctg-gcactg-3' and 5'-agcatcactgtgggtggcataggagc-3' in 60 mM Tris HCl (pH 10), 15 mM (NH$_4$)$_2$SO$_4$, 2 mM MgCl$_2$, 25 units/ml Taq Polymerase with 30 cycles annealing at 60° C. for 1 min., extension at 72° C. for 30 s, and 1 min. 95° C. denaturation.
Membrane Preparation Cells, cultured as above, were harvested and washed three times with cold PBS and frozen at −80° C. The pellet was resuspended in cold 20 mM HEPES-NaOH buffer containing 10 mM EDTA (pH 7.4), and homogenised with a polytron (Kinematica, AG, Littau, Switzerland) for 10 s at 10 000 rpm. After centrifugation for 30 min. at 4° C., the pellet was washed once with the same buffer, and once with cold 20 mM HEPES-NaOH buffer containing 0.1 mM EDTA, (pH 7.4). Protein content was measured using the micro BCA method from Pierce-Perbio (Rockford, Ill., USA) using bovine serum albumin as standard.
[$^3$H]-LY354740 Binding After thawing, the membranes were resuspended in cold 50 mM Tris-HCl buffer containing 2 mM MgCl$_2$ (pH 7) (binding buffer). The final concentration of the membranes in the assays was 25 µg protein/ml. Inhibition experiments were performed with membranes incubated with 10 nM [$^3$H]-LY354740 at room temperature, for 1 hour, in presence of various concentrations of the compound to be tested. Following the incubations, membranes were filtered onto Whatmann GF/B glass fiber filters and washed 5 times with cold binding buffer. Non specific binding was measured in the presence of 10 µM DCG IV. After transfer of the filters into plastic vials containing 10 ml of Ultima-gold scintillation fluid from Perkin-Elmer (Boston, Mass., USA), the radioactivity was measured by liquid scintillation in a Tri-Carb 2500 TR counter (Packard, Zütrich, Switzerland).
Data Analysis.

The inhibition curves were fitted with a four parameter logistic equation giving IC$_{50}$ values, and Hill coefficients.

EXAMPLES

Synthesis of Starting Material

Most of the starting material used in the general procedures I and II is commercially available. However some of said starting material has been prepared according to the procedures as outlined hereafter and unless otherwise specified, the intermediate compounds described therein are novel compounds. The rest of the starting material useful in the general procedures I and II may be prepared taking into account the following examples of preparation and using known methods:

Synthesis of Acetophenones Derivatives

Starting Material of Formula II

Example A.1

4-Methyl-3-trifluoromethyl-acetophenone

To a stirred and cooled (0° C.) solution of potassium tert.-butanolate (1.39 g, 12 mmol) in DMSO (3 ml) was added diethyl malonate (1.9 ml, 12 mmol) and the reaction mixture was stirred for 20 min at room temperature. To the white suspension was added at room temperature 4-fluoro-3-trifluoromethyl-acetophenone (1 g, 5 mmol) and DMSO (2 ml). The reaction mixture was stirred for 6 h at 60° C. and for 16 h at room temperature. The reaction mixture was cooled (0° C.), a solution of potassium hydroxide (1.09 g, 19 mmol) in water (2 ml) was added and the mixture was stirred at 100° C. for 23 h. The mixture was poured into ice/water (40 ml) and extracted with diethyl ether (2×40 ml). The combined organic layers were washed with water (3×30 ml), brine (30 ml), dried (MgSO$_4$) and evaporated. The crude product (0.92 g) was further purified by column chromatography on silica gel (heptane/ethyl acetate 3:1) to give the title compound (0.76 g, 77%) as a light yellow liquid. MS (EI) 202.0 [M].

Example A.2

4-Ethoxy-3-trifluoromethyl-acetophenone

To a stirred suspension of potassium ethanolate (2.36 g, 27 mmol) in ethanol (30 ml) was added at room temperature a solution of 4-fluoro-3-trifluoromethyl-acetophenone (2.5 g, 12 mmol) in ethanol (10 ml). The reaction mixture was stirred at 60° C. for 2 h and evaporated. Ice/2 N HCl (50 ml) was added and the water layer was extracted with diethylether (2×100 ml).

The combined organic layers were washed with ice-water (50 ml), brine (50 ml), dried (MgSO$_4$) and evaporated to give the title compound (2.9 g, 98%) as a brown solid, which was used without further purification. MS (EI) 232.1 [M].

Example A.3

4-(2,2,2-Trifluoro-ethoxy)-3-trifluoromethyl-acetophenone

To a stirred solution of 4-fluoro-3-trifluoromethyl-acetophenone (2.5 g, 12 mmol) in DMSO (15 ml) was added at room temperature 2,2,2-trifluoroethanol (1.7 g, 17 mmol) and potassium hydroxide (1.74 g, 27 mmol). The reaction mixture was stirred for 30 min at 40° C., ice/2N HCl (50 ml) was added and the water layer was extracted with diethylether (2×100 ml). The combined organic layers were washed with ice-water (50 ml), brine (50 ml), dried (MgSO$_4$) and evaporated to give the title compound (3.6 g, 98%) as a brown solid, which was used without further purification. MS (EI) 286.1 [M].

Example A.4

3-Methyl-4-trifluoromethyl-acetophenone

The 1-(3-methyl-4-trifluoromethyl-phenyl)-ethanone was prepared by the following sequence:

Step 1:
5-Methyl-2-nitro-4-trifluoromethyl-phenylamine

Under argon atmosphere, a suspension of potassium tert-butanolate (71.6 g, 625 mmol) in DMSO (150 mL) was placed in a 1.5 L flask, fitted with a mechanical stirrer. Then diethyl malonate (97.9 mL, 625 mmol) was added drop wise at 20-30° C. under ice bath cooling. To the thick white suspension was the added solid commercially available 5-chloro-2-nitro-4-trifluoromethyl-phenylamine [CAS-No. 35375-74-7] (60.14 g, 250 mmol) in one portion, the mixture was diluted with DMSO (100 mL) and the red solution warmed up to 60° C. and stirred for 20 h at 60° C. The mixture was cooled to 23° C. and a solution of potassium hydroxide (85%, 65.24 g, 1 mol) in water (100 mL) was added drop wise. The mixture was then heated to 100° C. and stirred for further 4 h. The mixture was cooled to 23° C., diluted with water (ca. 1000 mL), acidified with 37% HCl 3 to pH 3, and extracted three times with tert-butyl methyl ether (TBME) The organic layers were washed with brine, dried over MgSO$_4$ and evaporated to give a brown solid, which was triturated with hot heptane, filtered off and washed with heptane to give the title compound as a brown solid (50.0 g, 91%), which was used without further purification. MS (ISN) 218.9 [M−H].

Step 2:
1-Bromo-5-methyl-2-nitro-4-trifluoromethyl-benzene

To a rapidly stirred mixture of tert-butyl nitrite (45.33 mL, 382 mmol) and copper(II) bromide (76.1 g, 341 mmol) in acetonitrile (450 mL) at 65° C. was added cautiously solid 5-methyl-2-nitro-4-trifluoromethyl-phenylamine from step 1 (50.0 g, 227 mmol). After the addition was complete, stirring was continued for further 1 h at 65° C. The mixture was cooled to 23° C. and poured into 1 N HCl (1000 mL), extracted twice with TBME, the organic layer was washed with brine, dried over MgSO$_4$. Removal of the solvent in vacuum left a brown oil, which was purified by silica gel column chromatography with heptane/ethyl acetate 9:1 to give the title compound as a yellow liquid (49.8 g, 77%). MS (EI) 283.0 μl and 285.0 [M+2].

Step 3:
5-Methyl-2-nitro-4-trifluoromethyl-benzonitrile

A mixture of 1-bromo-5-methyl-2-nitro-4-trifluoromethyl-benzene from step 2 (49.80 g, 175 mmol) and copper(I) cyanide (16.5 g, 184 mmol) in 1-methyl-2-pyrrolidone (NMP) (180 mL) was heated up to 150° C. and stirred for 30 min under nitrogen atmosphere. The mixture was cooled to 23° C. and poured into 1 N HCl, extracted with TBME, washed with brine and dried over Na$_2$SO$_4$. Removal of the solvent in vacuum left a brown oil, which was purified by silica gel column chromatography with heptane/ethyl acetate 4:1->2:1 to give the title compound as a light yellow solid (35.48 g, 88%). MS (EI) 230.1 [M].

Step 4:
2-Amino-5-methyl-4-trifluoromethyl-benzonitrile

Iron powder (37.42 g, 670 mmol) was added in small portions to a stirred suspension of finely grinded 5-methyl-2-nitro-4-trifluoromethyl-benzonitrile from step 3 (34.58 g, 150 mmol) in methanol (75 mL) and 37% HCl (93 mL). The internal temperature was kept between 40 and 60° C. by external water bath cooling. The resulting brown solution was stirred for 1 h at 50° C., giving a green suspension. The mixture was poured into ice cold water (600 mL), the precipitated solid was filtered off and washed with water to give a green solid, which was dissolved in boiling ethanol (700 mL), activated carbon (ca. 10 g) was added and the mixture was refluxed for 1 h. The hot solution was filtered and the solvent was evaporated in vacuum to leave the title compound as a brown-yellow solid (23.55 g, 78%), which was used without further purification. MS (EI) 200.1 [M].

Step 5: 3-Methyl-4-trifluoromethyl-benzonitrile

To a solution of 2-amino-5-methyl-4-trifluoromethyl-benzonitrile from step 4 (23.34 g, 117 mmol) in dry THF (350 mL) was added isoamyl nitrite (34.3 mL, 257 mmol) and the mixture was refluxed for 20 h. Additional isoamyl nitrite (16.6 mL, 129 mmol) was added and the mixture was refluxed for further 20 h. The mixture was cooled to 23° C. and diluted with TBME, the organic layer was washed with 1 N HCl, sat. NaHCO$_3$-sol. and brine, dried over Na$_2$SO$_4$. Removal of the solvent in vacuum left a brown oil (25.82 g), which was purified by bulb to bulb distillation to give a yellow liquid (20.11 g), which was finally purified by distillation to give the title compound as a yellow liquid (17.10 g, 79%; bp 38-42° C. at 0.8 mbar). MS (EI) 185.1 [M].

Step 6: 3-Methyl-4-trifluoromethyl-benzoic Acid

A mixture of 3-methyl-4-trifluoromethyl-benzonitrile from step 5 (16.25 g, 88 mmol) and 3 N NaOH (88 mL, 264 mmol) in dioxane (90 mL) was refluxed for 18 h. The mixture was cooled to 23° C., diluted with TBME, acidified with 1 N HCl to pH 1 and extracted twice with TBME. The combined organic layers were washed with brine, dried over MgSO$_4$. Removal of the solvent in vacuum left the title compound as an off white solid (14.46 g, 81%), %), which was used without further purification. MS (ISN) 203.1 [M−H].

Step 7:
N-Methoxy-3,N-dimethyl-4-trifluoromethyl-benzamide

To a suspension of 3-methyl-4-trifluoromethyl-benzoic acid from step 6 (14.1 g, 69.1 mmol), N,O-dimethylhydroxylamine hydrochloride (10.78 g, 111 mmol), N-methylmorpholine (12.14 mL, 111 mmol) and 4-DMAP (844 mg, 691 mmol) in DCM (230 mL) at 0° C. were added 1-(3-dimethylaminopropyl)-3-ethylcarbodiimide hydrochloride (EDC) (15.98 g, 82.9 mmol) and DMF (85 mL). The mixture was warmed up to 23° C. and was stirred for 18 h under nitrogen atmosphere. The mixture was diluted with TBME, washed with water and twice brine, dried over $Na_2SO_4$. Removal of the solvent in vacuum left the title compound as a brown oil (16.92 g, 99%), which was used without further purification. MS (ISP) 248.0 [M+H].

Step 8:
1-(3-Methyl-4-trifluoromethyl-phenyl)-ethanone

To a solution of N-methoxy-3,N-dimethyl-4-trifluoromethyl-benzamide from step 7 (16.90 g, 68.36 mmol) in THF (280 mL) at −5° C. was added a 3 M methylmagnesium bromide solution in diethyl ether (45.6 mL, 136.7 mmol). The mixture was stirred at 0° C. for 1 h, then was warmed up to 23° C. and stirring was continued at 23° C. for further 1.5 h under nitrogen atmosphere. Then 1 N HCl (100 mL) was added drop wise to the mixture and stirring was continued for 30 min. The mixture was diluted with EtOAc and the aqueous layer was separated, the organic layer was washed with brine and dried over $MgSO_4$. Removal of the solvent in vacuum left the title compound as a light brown liquid (12.87 g, 93.1%), which was used without further purification. MS (EI) 202.1 [M].

Example A.5

3-Ethoxy-4-trifluoromethyl-acetophenone

The 1-(3-ethoxy-4-trifluoromethyl-phenyl)-ethanone was prepared by the following sequence:

Step 1:
5-Ethoxy-2-nitro-4-trifluoromethyl-phenylamine

To EtOH (500 mL) was added potassium metal (ca. 21 g, ca. 537 mmol) and the vigorous reaction had to be cooled with an ice bath. Stirring was continued until all potassium metal was dissolved. Solid commercially available 5-chloro-2-nitro-4-trifluoromethyl-phenylamine [CAS-No. 35375-74-7] (57.74 g, 240 mmol) was added in one portion and the resulting dark red mixture was stirred at 55-60° C. for 4 days. The warm reaction mixture was slowly poured into $H_2O$ (ca. 2000 mL), adjusted pH with conc. HCl to pH 2, the yellow precipitate was filtered off, washed with $H_2O$ and dried in air at 60° C. to give a yellow solid (57.81 g, 96%), which was used without further purification. MS (ISN) 249 [M−H].

Step 2:
1-Bromo-5-ethoxy-2-nitro-4-trifluoromethyl-benzene

Solid 5-ethoxy-2-nitro-4-trifluoromethyl-phenylamine from step 1 (57.81 g, 231 mmol) was added slowly over 15 min to a rapidly stirred mixture of tert-butyl nitrite (45.8 mL, 347 mmol) and anhydrous copper(II) bromide (77.4 g, 347 mmol) in acetonitrile (462 mL), which was heated to 65° C. in an oil bath. Stirring at 65° C. was continued for 30 min, the reaction mixture was cooled to 23° C., poured into 1 N HCl, saturated with solid NaCl, extracted with TBME, dried over $MgSO_4$. Removal of the solvent in vacuum left a dark brown oil (74.5 g). Silica gel column chromatography with heptane/EtOAc 4:1 gave the title compound as a yellow solid (63.03 g, 87%). MS (EI) 313.0 [M] and 315.0 [M+2].

Step 3:
5-Ethoxy-2-nitro-4-trifluoromethyl-benzonitrile

A mixture of 1-bromo-5-ethoxy-2-nitro-4-trifluoromethyl-benzene from step 2 (61.81 g, 197 mmol) and CuCN (18.51 g, 207 mmol) in NMP (197 mL) was heated to 150° C. for 30 min. Cooled to 23° C., poured into 1 N HCl, extracted with TBME, washed with brine, dried over $Na_2SO_4$. Removal of the solvent in vacuum left a brown oil. Silica gel column chromatography with heptane/EtOAc 4:1 gave the title compound as a yellow solid (46.73 g, 91%). MS (EI) 260.1 [M].

Step 4:
2-Amino-5-ethoxy-4-trifluoromethyl-benzonitrile

Iron powder (40.96 g, 733 mmol) was added in small portions over 5 min to a stirred suspension of finely grinded 5-ethoxy-2-nitro-4-trifluoromethyl-benzonitrile from step 3 (42.79 g, 164.5 mmol) in MeOH (85 mL) and conc. HCl (102 mL) with water bath cooling keeping the internal temperature at 40-50° C. The resulting mixture was stirred for further 1 h at ca. 50° C. and then poured into ice cold $H_2O$ (700 mL). The precipitate was filtered, washed with water, dried, and dissolved in boiling EtOH (800 mL), activated carbon (ca. 10 g) was added, the mixture was refluxed for 45 min, the hot solution was filtered and evaporated to dryness to leave a yellow solid (31.81 g, 84%), which was used without further purification. MS (EI) 230.1 [M].

Step 5: 3-Ethoxy-4-trifluoromethyl-benzonitrile

To a solution of 2-amino-5-ethoxy-4-trifluoromethyl-benzonitrile from step 4 (31.62 g, 137.4 mmol) in dry THF (410 mL) was added isoamyl nitrite (40.4 mL, 302 mmol) and the mixture was refluxed for 16 h. The solvent was removed in vacuum to give an orange oil, which was dissolved in sat. $NaHCO_3$-sol., extracted three times with diethyl ether. The combined organic layers were washed with 1 N HCl and brine, dried over $Na_2SO_4$. Removal of the solvent in vacuum left an orange oil, which was purified by double Kugelrohr distillation (up to 160° C. bath temperature at 1.5 mbar) to give the title compound as a light yellow solid (25.06 g, 85%). MS (EI) 185.1 μl.

Step 6:
1-(3-Ethoxy-4-trifluoromethyl-phenyl)-ethanone

To a solution of 3-ethoxy-4-trifluoromethyl-benzonitrile from step 5 (5.00 g, 23.2 mmol), copper(I) bromide (100 mg, 0.7 mmol), tert.-butyldimethylchlorosilane (4.20 g, 27.9 mmol) in dry THF (30 mL) at −70° C. was drop wise added a 3 M methylmagnesium bromide solution in diethyl ether (13.2 mL, 39.6 mmol). The mixture was stirred at −70° C. for 10 min, then was warmed up to 0° C. and stirring was continued at 0° C. for further 2 h under nitrogen atmosphere. Poured the reaction mixture onto ice and sat. $NH_4Cl$-sol., extracted three times with diethyl ether, washed the combined organic layers with brine, dried over $MgSO_4$. Removal of the solvent in vacuum left a brown oil, which was purified by silica gel column chromatography with heptane/EtOAc 4:1 to give the title compound as a yellow liquid (1.84 g, 34%). MS (EI) 232 [M].

Example A.6

3-(2,2,2-Trifluoro-ethoxy)-4-trifluoromethyl-acetophenone

The 1-[3-(2,2,2-trifluoro-ethoxy)-4-trifluoromethyl-phenyl]-ethanone was prepared by the following sequence:

Step 1: 2-Nitro-5-(2,2,2-trifluoro-ethoxy)-4-trifluoromethyl-phenylamine

Commercially available 5-chloro-2-nitro-4-trifluoromethyl-phenylamine [CAS-No. 35375-74-7] (72.2 g, 300 mmol) was dissolved in DMSO (600 mL) and 2,2,2-trifluoroethanol (270 mL) were added at 23° C., the slightly exothermic reaction was cooled with a ice bath. KOH (85%, 99.0 g, 1500 mmol) were added slowly and the dark red reaction mixture was stirred at 23° C. for 4 days. Transferred into a 3 L flask and 1500 ml $H_2O$ were added under ice bath cooling, acidified with 3 N HCl and stirred at 23° C. for 3 h, filtered off the yellow precipitate, washed with $H_2O$ and dried in air at 60° C. to give the title compound as a yellow solid (89.47 g, 98%). MS (ISN) 303.1 [M−H].

Step 2: 1-Bromo-2-nitro-5-(2,2,2-trifluoro-ethoxy)-4-trifluoromethyl-benzene Solid 2-nitro-5-(2,2,2-trifluoro-ethoxy)-4-trifluoromethyl-phenylamine from step 1 (24.28 g, 80 mmol) was added slowly over 15 min to a rapidly stirred mixture of tert-butyl nitrite (14.23 mL, 120 mmol) and anhydrous copper(II) bromide (26.75 g, 120 mmol) in acetonitrile (160 mL), which was heated to 65° C. in an oil bath. Stirring at 65° C. was continued for 2 h, the reaction mixture was cooled to 23° C., poured into 1 N HCl, saturated with solid NaCl, extracted with TBME, dried over $MgSO_4$. Removal of the solvent in vacuum left a dark brown oil (35.57 g). Silica gel column chromatography with heptane/EtOAc 4:1 gave the title compound as an orange solid (30.54 g, 104%), which was used without further purification. MS (EI) 367 [M] and 369 [M+2].

Step 3: 2-Nitro-5-(2,2,2-trifluoro-ethoxy)-4-trifluoromethyl-benzonitrile

A mixture of 1-bromo-2-nitro-5-(2,2,2-trifluoro-ethoxy)-4-trifluoromethyl-benzene from step 2 (30.54 g, 83.0 mmol) and CuCN (7.80 g, 87.1 mmol) in NMP (83 mL) was heated to 150° C. for 30 min. Cooled to 23° C., poured into 1 N HCl, extracted with EtOAc, washed with brine, dried over $Na_2SO_4$. Removal of the solvent in vacuum left a dark brown oil (33.9 g). Silica gel column chromatography with heptane/EtOAc 9:1->4:1 gave the title compound as a yellow solid (22.05 g, 85%). MS (EI) 314 [M].

Step 4: 2-Amino-5-(2,2,2-trifluoro-ethoxy)-4-trifluoromethyl-benzonitrile

Iron powder (15.80 g, 283.0 mmol) was added in small portions over 5 min to a stirred suspension of finely grinded 2-nitro-5-(2,2,2-trifluoro-ethoxy)-4-trifluoromethyl-benzonitrile from step 3 (19.93 g, 63.4 mmol) in MeOH (32 mL) and conc. HCl (40 mL) with water bath cooling keeping the internal temperature at 25-35° C. The resulting mixture was stirred for further 1 h at ca. 30° C. and then poured into ice cold $H_2O$ (400 mL). The precipitate was filtered, washed with water, dried, and dissolved in boiling EtOH (400 mL), activated carbon (ca. 10 g) was added, the mixture was refluxed for 45 min, the hot solution was filtered and evaporated to dryness to leave a dark green solid (15.96 g, 84%), which was further purified by silica gel column chromatography with heptane/EtOAc 4:1 to give the title compound as a yellow solid (14.56 g, 81%). MS (ISN) 283 [M−H].

Step 5: 3-(2,2,2-Trifluoro-ethoxy)-4-trifluoromethyl-benzonitrile

To a solution of 2-amino-5-(2,2,2-trifluoro-ethoxy)-4-trifluoromethyl-benzonitrile from step 4 (14.47 g, 50.9 mmol) in dry THF (153 mL) was added isoamyl nitrite (15.0 mL, 112.0 mmol) and the mixture was refluxed for 20 h. The solvent was removed in vacuum to give an orange oil, which was dissolved in TBME, washed with 1 N HCl, sat. $NaHCO_3$-sol. and brine, dried over $Na_2SO_4$. Removal of the solvent in vacuum left a brown solid (15.05 g), which was purified by Kugelrohr distillation (up to 155° C. bath temperature at 1.2 mbar) to give the title compound as a light yellow solid (10.83 g, 79%). MS (EI) 269 [M].

Step 6: 3-(2,2,2-Trifluoro-ethoxy)-4-trifluoromethyl-benzoic Acid

A mixture of 3-(2,2,2-trifluoro-ethoxy)-4-trifluoromethyl-benzonitrile from step 5 (8.75 g, 33 mmol) and 3 M NaOH (3.9 g, 98 mmol in 33 mL $H_2O$) in dioxane (33 mL) was refluxed for 7.5 h. Poured onto ice, acidified with conc. HCl to pH 1, saturated with solid NaCl, extracted with TBME, dried over $MgSO_4$. Removal of the solvent in vacuum left the title compound as an off-white solid (9.22 g, 98%), %), which was used without further purification. MS (ISN) 286.9 [M−H].

Step 7: N-Methoxy-N-methyl-3-(2,2,2-trifluoro-ethoxy)-4-trifluoromethyl-benzamide To a mixture of 3-(2,2,2-trifluoro-ethoxy)-4-trifluoromethyl-benzoic acid from step 6 (9.22 g, 32 mmol), N,O-dimethylhydroxylamine hydrochloride (5.00 g, 51 mmol), N-methylmorpholine (5.62 mL, 51 mmol) and 4-DMAP (391 mg, 3.2 mmol) in DCM (100 mL) and DMF (20 mL) at 0° C. was added 1-(3-dimethylaminopropyl)-3-ethylcarbodiimide hydrochloride (EDC) (7.36 g, 38 mmol) and the mixture was stirred at 23° C. for 18 h. Poured onto ice cold 1 N HCl, extracted with TBME, washed with sat. $NaHCO_3$-sol. and brine, dried over $Na_2SO_4$. Removal of the solvent in vacuum left the title compound as a brown oil (10.555 g, 100%), %), which was used without further purification. MS (EI) 331.0 [M].

Step 8: 1-[3-(2,2,2-Trifluoro-ethoxy)-4-trifluoromethyl-phenyl]-ethanone

To a solution of N-methoxy-N-methyl-3-(2,2,2-trifluoro-ethoxy)-4-trifluoromethyl-benzamide from step 7 (10.467 g, 32 mmol) in THF (100 mL) at −5° C. was added methylmagnesium bromide (3 M in $Et_2O$, 21.1 mL, 64 mmol). The mixture was stirred at 0° C. for 15 min, then warmed up to 23° C., stirring was continued for further 1.5 h at 23° C. Cooled to 0° C., 1 N HCl (150 mL) was added dropwise, stirring was continued at 23° C. for 15 min, the mixture was diluted with TBME, the phases were separated, the organic layer was washed with water and brine, dried over $MgSO_4$. Removal of the solvent in vacuum left a yellow solid (9.021 g, 100%), which was used without further purification. MS (EI) 286.1 [M].

Synthesis of Intermediates Compounds

N-Hydroxy-Amidines of Formulae (VIII) and (IX)

Example B.1

N-Hydroxy-7-trifluoromethyl-5-(4-trifluoromethyl-phenyl)-pyrazolo[1,5-a]pyrimidine-3-carboxamidine A stirred mixture of 7-trifluoromethyl-5-(4-trifluoromethyl-phenyl)-pyrazolo[1,5-a]pyrimidine-3-carbonitrile [CAS-No. 851262-50-5] (2.0 g, 5.61 mmol), hydroxylamine hydrochloride (0.78 g, 11.2 mmol) and potassium carbonate (2.33 g, 16.8 mmol) in ethanol (100 ml) was heated under reflux conditions for 3 h. After the reaction mixture reached room temperature the precipitate was collected by filtration and washed with ethanol and ethyl acetate. The combined filtrates were evaporated and the crude product purified by flash chromatography on silica gel (ethyl acetate/heptane) to yield the title compound (1.51 g, 69%) as an orange solid. MS (ISP) 389.9 [(M+H)$^+$]; mp 252° C.

Example B.2

N-Hydroxy-5-sulfamoyl-thiophene-2-carboxamidine

A stirred mixture of 5-sulfamoyl-thiophene-2-carbonitrile [CAS-No. 519055-65-3] (0.31 g, 1.65 mmol), hydroxylamine hydrochloride (0.23 g, 3.31 mmol) and sodium carbonate (0.175 g, 1.65 mmol) in water (4.6 ml) and ethanol (1 ml) was heated under reflux conditions for 1.5 h. The reaction mixture was poured into water (50 ml) and extracted with ethyl acetate (3×100 ml). The combined organic layers were washed with brine (100 ml), dried (MgSO$_4$) and evaporated. The crude product was purified by flash chromatography on silica gel (ethyl acetate/heptane) and crystallization (ethyl acetate/MeOH/hexane) to yield the title compound (0.21 g, 58%) as a white solid. MS (ISN) 220.1 [(M−H)$^−$]; mp 189° C.

Example B.3

N-Hydroxy-4-trifluoromethyl-2-(4-trifluoromethyl-phenyl)-imidazo[1,5-a]pyrimidine-8-carboxamidine A stirred mixture of 4-trifluoromethyl-2-(4-trifluoromethyl-phenyl)-imidazo[1,5-a]pyrimidine-8-carbonitrile [CAS-No. 851263-42-8] 1.16 g, 3.26 mmol), hydroxylamine hydrochloride (0.46 g, 6.62 mmol) and potassium carbonate (1.35 g, 9.77 mmol) in ethanol (50 ml) was heated under reflux conditions for 3 h. The precipitate was collected by filtration and washed with ethanol, the combined filtrates were evaporated and the crude product purified by column chromatography on silica gel (ethyl acetate/ethanol 95:5) and crystallization from diethyl ether/hexane to yield the title compound (257 mg, 20%) as a red solid. MS (ISN) 388.2 [(M−H)$^−$]; mp 213° C.

Example B.4

6-Amino-N-hydroxy-nicotinamidine

A stirred mixture of commercially available 2-amino-5-cyano-pyridine [CAS-No. 4214-73-7] (5.0 g, 42 mmol), hydroxylamine hydrochloride (17.5 g, 0.25 mol) and sodium carbonate (31.1 g, 0.29 mol) in water (95 ml) and ethanol (21 ml) was heated under reflux conditions for 6 h. The reaction mixture was poured into water (150 ml) and extracted with ethyl acetate (4×100 ml). The combined organic layers were washed with brine (150 ml), dried (MgSO$_4$) and evaporated. The crude product was purified by column chromatography on silica gel (ethyl acetate/MeOH/NH$_4$OH 4:1:0.5) and crystallization (ethyl acetate/MeOH/hexane) to yield 6-amino-nicotinamide (1.39 g) and the title compound (1.42 g, 22%) as an off-white solid. MS (EI) 152.1 [(M)$^+$]; mp 300° C.

Example B.5

2-Amino-N-hydroxy-pyrimidine-5-carboxamidine

A stirred mixture of commercially available 2-amino-5-cyano-pyrimidine [CAS-No. 1753-48-6] (1.39 g, 11.6 mmol), hydroxylamine hydrochloride (1.61 g, 23.2 mol) and potassium carbonate (4.8 g, 34.7 mol) in ethanol (57 ml) was heated under reflux conditions for 3 h. The reaction mixture was evaporated and purified by column chromatography on silica gel (dichloromethane/MeOH 9:1) to yield the title compound (1.28 g, 72%) as an off-white solid. MS (EI) 153.1 [(M)$^+$]; mp 218° C.

Example B.6

2-Amino-N-hydroxy-pyridine-4-carboxamidine

A stirred mixture of commercially available 2-amino-4-cyano-pyridine [CAS-No. 42182-27-4] (1.0 g, 8.39 mmol), hydroxylamine hydrochloride (1.17 g, 16.8 mmol) and sodium carbonate (0.89 g, 8.39 mol) in water (8 ml) and ethanol (16 ml) was heated under reflux conditions for 3 h. The reaction mixture was evaporated, water (10 ml) was added and the mixture stirred at room temperature for 1 h. The precipitate was collected by filtration to yield the title compound (0.87 g, 68%) as an off-white solid. MS (EI) 152.0 [(M)$^+$]; mp 188° C.

Synthesis of Intermediates Compounds

Pyrazolo-Pyrimidine Carboxylic Acids (Intermediates of Formula VI) from Acetophenones Some of the intermediates compounds, e.g. the pyrazolo-pyrimidine carboxylic acids derivatives which can be used according to the general procedures I and II are commercially available. However some of said intermediates have been prepared from acetophenones according to the procedures as outlined hereafter and unless otherwise specified, these compounds are novel. The person skilled in the art will be able to prepare other pyrazolo-pyrimidine carboxylic acids derivatives useful in the general procedures I and II taking into account the following examples of preparation:

Example C.1

7-Difluoromethyl-5-(4-trifluoromethyl-phenyl)-pyrazolo[1,5-a]pyrimidine-3-carboxylic Acid a) To a stirred solution of ethyl difluoroacetate (5.0 ml, 21 mmol) in tert-butyl-methyl-ether (30 ml) was added at room temperature a 5.4M solution of sodium methanolate in methanol (4.65 ml, 25 mmol) followed by a solution of commercially available 4-trifluoromethyl-acetophenone (4.0 g, 21 mmol) in tert-butyl-methyl-ether (10 ml). The reaction mixture was stirred at room temperature for 19 h, poured into ice/water (50 ml), acidified with 2N HCl (40 ml) and extracted with diethyl ether (2×100 ml). The combined organic layers were washed with brine (2×50 ml), dried (MgSO$_4$) and evaporated to give crude 4,4-difluoro-1-(4-trifluoromethyl-phenyl)-butane-1,3-dione (5.87 g) as a yellow liquid, which was used without further purification.

b) A stirred mixture of commercially available 3-amino-4-ethoxycarbonyl-pyrazole (3.38 g, 22 mmol) and 4,4-difluoro-1-(4-trifluoromethyl-phenyl)-butane-1,3-dione (5.8 g, 22 mmol) in acetic acid (45 ml) was heated under reflux conditions for 1.5 h. The reaction mixture was evaporated and the crude product (yellow solid, 8.5 g, 22 mmol) was dissolved in a mixture of 2M KOH in methanol (176.5 ml, 0.35 mol) and water (85 ml). The reaction mixture was stirred at 60° C. for 1.5 h, poured into ice/water (200 ml), acidified with 3N sulfuric acid (pH=4) and stirred at room temperature for 30 min. The precipitate was collected by filtration and further purified by crystallization from diethylether/methanol to give the title compound (4.51 g, 57%) as an off-white solid. MS (ISP) 356.1 [(M–H)⁻]; m.p. 261° C.

Example C.2

7-Trifluoromethyl-5-(4-trifluoromethyl-phenyl)-pyrazolo[1,5-a]pyrimidine-3-carboxylic Acid The title compound was prepared from commercially available ethyl trifluoroacetate, commercially available 4-trifluoromethyl-acetophenone and commercially available 3-amino-4-ethoxycarbonyl-pyrazole according to the general procedure I. Light yellow solid. MS (EI) 374.9 [M]; mp 248° C.

Example C.3

5-(4-Chloro-phenyl)-7-difluoromethyl-pyrazolo[1,5-a]pyrimidine-3-carboxylic acid The title compound was prepared from commercially available ethyl difluoroacetate, commercially available 4-chloro-acetophenone and commercially available 3-amino-4-ethoxycarbonyl-pyrazole according to the general procedure I. Off-white solid. MS (ISP) 322.2 [(M–H)⁻]; mp 232° C.

Example C.4

5-(4-Chloro-phenyl)-7-trifluoromethyl-pyrazolo[1,5-a]pyrimidine-3-carboxylic acid The title compound was prepared from commercially available ethyl trifluoroacetate, commercially available 4-chloro-acetophenone and commercially available 3-amino-4-ethoxycarbonyl-pyrazole according to the general procedure I. Off-white solid. MS (ISP) 340.0 [(M–H)⁻]; mp 238° C.

Example C.5

7-Difluoromethyl-5-(3-methyl-4-trifluoromethyl-phenyl)-pyrazolo[1,5-a]pyrimidine-3-carboxylic acid The title compound was prepared from commercially available ethyl difluoroacetate, 3-methyl-4-trifluoro-acetophenone (example A.4) and commercially available 3-amino-4-ethoxycarbonyl-pyrazole according to the general procedure I. Off-white solid. MS (ISP) 370.1 [(M–H)⁻]; mp 217° C.

Example C.6

5-(4-Chloro-3-methyl-phenyl)-7-trifluoromethyl-pyrazolo[1,5-a]pyrimidine-3-carboxylic acid The title compound was prepared from commercially available ethyl trifluoroacetate, commercially available 4-chloro-3-methyl-acetophenone and commercially available 3-amino-4-ethoxycarbonyl-pyrazole according to the general procedure I. Off-white solid. MS (ISP) 354.0 [(M–H)⁻]; mp 243° C.

Example C.7

5-(3,4-Dichloro-phenyl)-7-difluoromethyl-pyrazolo[1,5-a]pyrimidine-3-carboxylic acid The title compound was prepared from commercially available ethyl difluoroacetate, commercially available 3,4-dichloro-acetophenone and commercially available 3-amino-4-ethoxycarbonyl-pyrazole according to the general procedure I. Off-white solid. MS (ISP) 356.0 [(M–H)⁻]; mp 263° C.

Example C.8

5-(3-Methyl-4-trifluoromethyl-phenyl)-7-trifluoromethyl-pyrazolo[1,5-a]pyrimidine-3-carboxylic Acid The title compound was prepared from commercially available ethyl trifluoroacetate, 3-methyl-4-trifluoro-acetophenone (example A.4) and commercially available 3-amino-4-ethoxycarbonyl-pyrazole according to the general procedure I. Off-white solid. MS (ISP) 388.1 [(M–H)⁻]; mp 250° C.

Example C.9

5-(3,4-Dichloro-phenyl)-7-trifluoromethyl-pyrazolo[1,5-a]pyrimidine-3-carboxylic acid The title compound was prepared from commercially available ethyl trifluoroacetate, commercially available 3,4-dichloro-acetophenone and commercially available 3-amino-4-ethoxycarbonyl-pyrazole according to the general procedure I. Light yellow solid. MS (ISP) 374.1 [(M–H)⁻]; mp 264° C.

Example C.10

5-[3-(2,2,2-Trifluoro-ethoxy)-4-trifluoromethyl-phenyl]-7-trifluoromethyl-pyrazolo[1,5-a]pyrimidine-3-carboxylic acid The title compound was prepared from commercially available ethyl trifluoroacetate, 3-(2,2,2-trifluoroethoxy-4-trifluoro-acetophenone (Example A.6) and commercially available 3-amino-4-ethoxycarbonyl-pyrazole according to the general procedure I. Off-white solid. MS (ISP) 471.9 [(M–H)⁻]; mp 264° C.

Example C.11

5-(3-Ethoxy-4-trifluoromethyl-phenyl)-7-trifluoromethyl-pyrazolo[1,5-a]pyrimidine-3-carboxylic acid The title compound was prepared from commercially available ethyl trifluoroacetate, 3-ethoxy-4-trifluoro-acetophenone (Example A.5) and commercially available 3-amino-4-ethoxycarbonyl-pyrazole according to the general procedure I. Off-white solid. MS (ISP) 418.0 [(M–H)$^-$]; mp 264° C.

Example C.12

7-Difluoromethyl-5-(3-ethoxy-4-trifluoromethyl-phenyl)-pyrazolo[1,5-a]pyrimidine-3-carboxylic Acid The title compound was prepared from commercially available ethyl difluoroacetate, 3-ethoxy-4-trifluoro-acetophenone (Example A.5) and commercially available 3-amino-4-ethoxycarbonyl-pyrazole according to the general procedure I. Yellow solid. MS (ISP) 400.2 [(M–H)$^-$]; mp 247° C.

Example C.13

5-(4-Chloro-3-methyl-phenyl)-7-difluoromethyl-pyrazolo[1,5-a]pyrimidine-3-carboxylic acid The title compound was prepared from commercially available ethyl difluoroacetate, commercially available 4-chloro-3-methyl-acetophenone and commercially available 3-amino-4-ethoxycarbonyl-pyrazole according to the general procedure I. Light yellow solid. MS (ISP) 336.0 [(M–H)$^-$]; mp 238° C.

Example C.14

7-Difluoromethyl-5-[3-(2,2,2-trifluoro-ethoxy)-4-trifluoromethyl-phenyl]-pyrazolo[1,5-a]pyrimidine-3-carboxylic Acid The title compound was prepared from commercially available ethyl difluoroacetate, 3-(2,2,2-trifluoroethoxy-4-trifluoro-acetophenone (Example A.6) and commercially available 3-amino-4-ethoxycarbonyl-pyrazole according to the general procedure I. Off-white solid. MS (ISP) 454.2 [(M–H)$^-$]; mp 261° C.

Example C.15

5-(3-Chloro-4-trifluoromethyl-phenyl)-7-difluoromethyl-pyrazolo[1,5-a]pyrimidine-3-carboxylic Acid The title compound was prepared from commercially available ethyl difluoroacetate, 3-chloro-4-trifluoromethyl-acetophenone [CAS-No. 129322-80-1] and commercially available 3-amino-4-ethoxycarbonyl-pyrazole according to the general procedure I.
Light red solid. MS (ISP) 390.2 [(M–H)$^-$]; mp 216° C.

Example C.16

7-Difluoromethyl-5-(3-fluoro-4-trifluoromethyl-phenyl)-pyrazolo[1,5-a]pyrimidine-3-carboxylic Acid The title compound was prepared from commercially available ethyl difluoroacetate, commercially available 3-fluoro-4-trifluoromethyl-acetophenone and commercially available 3-amino-4-ethoxycarbonyl-pyrazole according to the general procedure I.
Light brown solid. MS (ISP) 374.1 [(M–H)$^-$]; mp 233° C.

Example C.17

5-(3-Chloro-4-trifluoromethyl-phenyl)-7-trifluoromethyl-pyrazolo[1,5-a]pyrimidine-3-carboxylic acid The title compound was prepared from commercially available ethyl trifluoroacetate, 3-chloro-4-trifluoromethyl-acetophenone [CAS-No. 129322-80-1] and commercially available 3-amino-4-ethoxycarbonyl-pyrazole according to the general procedure I.
Light yellow solid. MS (ISP) 408.0 [(M–H)$^-$]; mp 244° C.

Example C.18

5-(3-Fluoro-4-trifluoromethyl-phenyl)-7-trifluoromethyl-pyrazolo[1,5-a]pyrimidine-3-carboxylic Acid The title compound was prepared from commercially available ethyl trifluoroacetate, commercially available 3-fluoro-4-trifluoromethyl-acetophenone and commercially available 3-amino-4-ethoxycarbonyl-pyrazole according to the general procedure I.
Light yellow solid. MS (ISP) 392.0 [(M–H)$^-$]; mp 212° C.

Example C.19

5-(4-Trifluoromethoxy-phenyl)-7-trifluoromethyl-pyrazolo[1,5-a]pyrimidine-3-carboxylic Acid The title compound was prepared from commercially available ethyl trifluoroacetate, commercially available 4-trifluoromethoxy-acetophenone and commercially available 3-amino-4-ethoxycarbonyl-pyrazole according to the general procedure I.
White solid. MS (ISP) 390.0 [(M–H)$^-$]; mp 225° C.

Example C.20

7-Difluoromethyl-5-(4-trifluoromethoxy-phenyl)-pyrazolo[1,5-a]pyrimidine-3-carboxylic acid The title compound was prepared from commercially available ethyl difluoroacetate, commercially available 4-trifluoromethoxy-acetophenone and commercially available 3-amino-4-ethoxycarbonyl-pyrazole according to the general procedure I.
Off-white solid. MS (ISP) 372.1 [(M–H)$^-$]; mp 231° C.

Example C.21

5-(3,4-Difluoro-phenyl)-7-trifluoromethyl-pyrazolo[1,5-a]pyrimidine-3-carboxylic acid The title compound was prepared from commercially available ethyl trifluoroacetate, commercially available 3,4-difluoro-acetophenone and commercially available 3-amino-4-ethoxycarbonyl-pyrazole according to the general procedure I.
Light yellow solid. MS (ISP) 342.0 [(M–H)$^-$]; mp 274° C.

Example C.22

5-(4-Chloro-phenyl)-pyrazolo[1,5-a]pyrimidine-3-carboxylic acid a. A mixture of ethyl 3-(4-chloro-phenyl)-3-oxo-propionate (18.1 g, 0.080 mol) and ethyl 5-amino-1H-pyrazole-4- carboxylate (13.7 g, 0.088 mol) was stirred at for 3 h 160° C. Ethyl acetate (40 mL) and hexane (40 mL) were successively added to the cooled mixture and stirring was continued at 0° C. for 0.5 h. The crystals were isolated by filtration and triturated for 1.2 h with 0.2 N HCl (80 mL). The solid was filtered off, washed with water and dried to give ethyl 5-(4-chloro-phenyl)-7-hydroxy-pyrazolo[1,5-a]pyrimidine-3-carboxylate (13.3 g, 52%). White solid. MS (ISN) 316.3 [(M−H)⁻]; mp 190-192° C.

b. A mixture of 5-(4-chloro-phenyl)-7-hydroxy-pyrazolo[1,5-a]pyrimidine-3-carboxylate (9.53 g, 0.03 mol), phosphorous oxychloride (11.0 mL, 0.12 mol), and N,N-dimethylaniline (1.3 mL, 0.01 mol) was stirred for 2 h at 100° C. The mixture was evaporated in vacuo and the residue was partitioned between water and dichloromethane. The organic phase was washed with water, dried ($Na_2SO_4$) and evaporated in vacuo. The remaining solid was crystallized from ethyl acetate/hexane to give 7-chloro-5-(4-chloro-phenyl)-pyrazolo[1,5-a]pyrimidine (6.80 g, 67%). Pale-yellow solid, MS (ISP) 336.0 [(M+H)⁺]; mp 133-135° C.

c. A mixture of 7-chloro-5-(4-chloro-phenyl)-pyrazolo[1,5-a]pyrimidine (0.34 g, 1.0 mmol), triethylamine (0.28 mL, 2.0 mmol), and 5% palladium-charcoal (0.03 g) in ethanol (60 mL) was stirred in an atmosphere of hydrogen for 12 min at 20° C. The catalyst was removed by filtration and the solution was evaporated. The residue was partitioned between ethyl acetate and water and the organic layer was dried ($Na_2SO_4$) and evaporated in vacuo. The residue was crystallized from ethyl acetate/cyclohexane to give ethyl 5-(4-chloro-phenyl)-pyrazolo[1,5-a]pyrimidine-3-carboxylate (0.18 g, 59%). Off-white solid; MS (ISP) 301.9 [(M+H)⁺].

d. A mixture of ethyl 5-(4-chloro-phenyl)-pyrazolo[1,5-a]pyrimidine-3-carboxylate (0.12 g, 0.4 mmol) and 0.5 N sodium hydroxide solution (4 mL) in methanol (4 mL) was heated to 70° C. for 2 h. The mixture was cooled, diluted with water (8 mL) and concentrated in vacuo. The aqueous solution was acidified to pH 2 by the addition of 3N HCl. The precipitate was isolated by filtration, washed with water, and dried to give 5-(4-chloro-phenyl)-pyrazolo[1,5-a]pyrimidine-3-carboxylic acid (0.11 g, 100%). Off-white solid. MS (ISN) 272.3 [(M−H)⁻]; mp 309-311° C.

Example C.23

5-(4-Trifluoromethyl-phenyl)-pyrazolo[1,5-a]pyrimidine-3-carboxylic acid

By subjecting ethyl 3-(4-trifluoro-phenyl)-3-oxo-propionate in analogous manner to the procedures described in example C.22, steps a-d, the title compound was obtained. White solid. NMR (DMSO-$d_6$): δ 7.97/8.52 (2 d, 2×2H), 7.98/9.41 (2 d, 2×1H), 8.63 (s, 1H), 12.46 (s, 1H) ppm.

Example C.24

5-(4-Chloro-phenyl)-7-methyl-pyrazolo[1,5-a]pyrimidine-3-carboxylic acid

To a solution of 7-chloro-5-(4-chloro-phenyl)-pyrazolo[1,5-a]pyrimidine (0.34 g, 1.0 mmol) and tetrakis(triphenylphosphin)palladium (0.35 g, 0.3 mmol) in THF (15 mL) was added at 20° C. 2 M dimethylzinc/toluene solution (1.3 mL, 3.6 mmol) and the mixture was refluxed in an atmosphere of argon for 2 h. After the slow addition at 0° C. of sat. aqueous ammonium chloride solution (10 mL), the mixture was partitioned between ethyl acetate and water. The organic layer was evaporated in vacuo and the residue chromatographed on silica gel using ethyl acetate/hexane (1:2 v/v) as eluent to give ethyl 5-(4-chloro-phenyl)-7-methyl-pyrazolo[1,5-a]pyrimidine-3-carboxylate (0.15 g) as a white solid. This material was saponified using in an analogous manner the procedure described in example C.22, step d), to give the title compound. White solid; MS (ISN) 286.0 [(M−H)⁻]; mp 233-235° C.

Example C.25

7-Methyl-5-(4-trifluoromethyl-phenyl)-pyrazolo[1,5-a]pyrimidine-3-carboxylic acid Subjecting ethyl 3-(4-trifluoro-phenyl)-3-oxo-propionate in analogous manner to the procedures described in Example C.22, steps a-b, and applying to the resulting product the procedure described in example C.24, afforded the title compound. White solid. MS (ISP) 320.3 [(M−H)⁻]; mp 244-245° C.

Example C.26

5-(4-Chloro-phenyl)-7-ethyl-pyrazolo[1,5-a]pyrimidine-3-carboxylic acid

To a solution of 7-chloro-5-(4-chloro-phenyl)-pyrazolo[1,5-a]pyrimidine (1.0 g, 3.0 mmol), tetrakis(triphenylphosphin)palladium (0.35 g, 0.3 mmol) in THF (5 mL) was added at 20° C. 0.4 M ethylzinc chloride/THF solution (30 mL, 12 mmol; freshly prepared by stirring a mixture of 6 mL of 2 M ethylmagnesium chloride/THF and 24 mL of 0.5 M zinc chloride/THF for 1 h at 0° C. followed by 1 h at 20° C.) and the mixture was refluxed in an atmosphere of argon for 2 h. After the slow addition at 0° C. of sat. aqueous ammonium chloride solution (8 mL), the mixture was partitioned between ethyl acetate and 10% sodium chloride solution. The organic layer was evaporated in vacuo and the residue chromatographed on silica gel using ethyl acetate/cyclo-hexane (1:4 v/v) as eluent to give ethyl 5-(4-chloro-phenyl)-7-ethyl-pyrazolo[1,5-a]pyrimidine-3-carboxylic acid (0.53 g, 54%). This material was saponified using in an analogous manner the procedure described in example C.22, step d), to give the title compound. White solid; MS (ISN) 330.1 [(M−H)⁻]; mp 227° C.

Example C.27

5-(4-Chloro-phenyl)-7-propyl-pyrazolo[1,5-a]pyrimidine-3-carboxylic acid

Subjecting ethyl 7-chloro-5-(4-chloro-phenyl)-pyrazolo[1,5-a]pyrimidine in analogous manner to the procedure described in Example C.26, but replacing the ethylzinc chloride/THF solution by a 0.4 M propylzinc chloride/THF solution (freshly prepared from ethylmagnesium chloride and zinc chloride), the title compound was obtained. White solid. MS (ISN) 314.1 [(M−H)⁻]; mp 208° C.

Example C.28

5-(4-Chloro-phenyl)-7-cyclopropyl-pyrazolo[1,5-a]pyrimidine-3-carboxylic acid

To a solution of 7-chloro-5-(4-chloro-phenyl)-pyrazolo[1,5-a]pyrimidine (4.0 g, 12.0 mmol), tetrakis(triphenylphosphin)palladium (1.15 g, 1.0 mmol) in THF (20 mL) was added at 20° C. 0.25 M cyclopropylzinc chloride/THF suspension (ca.192 mL, 48 mol; freshly prepared by stirring a mixture of 96 mL of 0.5 M cyclopropylmagnesium bromide/THF and 96 mL of 0.5 M zinc chloride/THF (96 mL) for 1 h at 0° C. followed by 1 h at 20° C.) and the mixture was refluxed in an atmosphere of argon for 2.5 h. After the slow addition at 0° C. of sat. aqueous ammonium chloride solution (30 mL), the mixture was partitioned between ethyl acetate and 10% sodium chloride solution. The organic layer was evaporated in vacuo and the residue chromatographed on silica gel using ethyl acetate/cyclohexane (1:4 v/v) as eluent to give after crystallization from ethyl acetate ethyl 5-(4-chloro-phenyl)-7-cyclopropyl-pyrazolo[1,5-a]pyrimidine-3-carboxylic acid (2.54 g, 62%) as an off-white solid, mp 141-143° C. This material was saponified using in an analogous manner the procedure described in example C.22, step d), to give the title compound. Off-white solid, MS (ISN) 312.3 [(M–H)$^-$]; mp 242-243° C.

Example C.29

7-Cyclopropyl-5-(4-trifluoromethyl-phenyl)-pyrazolo[1,5-a]pyrimidine-3-carboxylic acid By subjecting ethyl 3-(4-trifluoro-phenyl)-3-oxo-propionate in analogous manner to the procedures described in example C.22, steps a-b, and applying to the resulting product the procedure described in example C.28, the title compound was obtained. Off-white solid. MS (ISP) 346.3 [(M–H)$^-$]; mp 233-235° C.

Example C.30

4-Trifluoromethyl-2-(4-trifluoromethyl-phenyl)-imidazo[1,5-a]pyrimidine-8-carboxylic acid 1) A stirred solution of commercially available 5-amino-1H-imidazole-4-carboxamide (25 g, 198 mmol) in methanesulfonic acid (107 ml) and ethanol (400 ml) was stirred at reflux conditions for 12d, evaporated and water (300 ml) was added. While stirring and cooling (ice/water) sodium hydroxide solution (32%) was added until pH=6 was reached. The water layer was saturated with sodium chloride and extracted with ethyl acetate (3×200 ml). The combined organic layers were dried (MgSO$_4$), evaporated and the crude product purified crystallization (ethyl acetate/ethanol) to yield 5-amino-1H-imidazole-4-carboxylic acid ethyl ester (13.7 g, 45%) as a light brown solid. MS (EI) 155.1 [(M)$^+$]; mp 178° C.

2) A mixture of 4,4,4-trifluoro-1-(4-trifluoromethyl-phenyl)-butane-1,3-dione (10.0 g, 35.2 mmol) and 5-amino-1H-imidazole-4-carboxylic acid ethyl ester (5.0 g, 32.2 mmol) in acetic acid (120 ml) was refluxed for 24 h and evaporated. The crude product was further purified by column chromatography on silica gel (ethyl acetate/heptane) and crystallization (diethyl acetate/hexane) to yield 4-trifluoromethyl-2-(4-trifluoromethyl-phenyl)-imidazo[1,5-a]pyrimidine-8-carboxylic acid ethyl ester (5.65 g, 43%) as a yellow solid. MS (EI) 403.1 [(M)$^+$]; mp 243° C.

3) A mixture of 4-trifluoromethyl-2-(4-trifluoromethyl-phenyl)-imidazo[1,5-a]pyrimidine-8-carboxylic acid ethyl ester (5.6 g, 13.9 mmol), 2M potassium hydroxide solution (111 ml) and water (55 ml) was stirred at room temperature for 5 h, cooled (ice-water), and acetic acid (30 ml) was added. The mixture was evaporated, acetic acid (150 ml) was added and the stirred solution was heated under reflux conditions for 20 min. The reaction mixture was evaporated, water (150 ml) was added followed by extraction with ethyl acetate (2×300 ml). The combined organic layers were washed with brine (2×150 ml), dried (MgSO$_4$) and evaporated. The crude product was further purified by column chromatography on silica gel (ethyl acetate/heptane 1:1) to yield 4-trifluoromethyl-2-(4-trifluoromethyl-phenyl)-imidazo[1,5-a]pyrimidine-8-carboxylic acid (1.93 g, 37%) as a yellow solid. MS (ISN) 374.3 [(M–H)$^-$]; mp 231° C.

Example C.31

7-Trifluoromethyl-5-(3-trifluoromethyl-phenyl)-pyrazolo[1,5-a]pyrimidine-3-carboxylic Acid The title compound was prepared from commercially available ethyl trifluoroacetate, commercially available 3-trifluoromethyl-acetophenone and commercially available 3-amino-4-ethoxycarbonyl-pyrazole according to the general procedure I. Light yellow solid. MS (EI) 375.0 [(M)$^+$]; mp 212° C.

Example C.32

8-Trifluoromethyl-6-(4-trifluoromethyl-phenyl)-imidazo[1,2-a]pyridine-3-carboxylic Acid Step 1) (4-Methoxy-benzyl)-(3-trifluoromethyl-pyridin-2-yl)-amine A mixture of 2-chloro-3-trifluoromethylpyridine (64.83 g, 357 mmol), 4-methoxybenzylamine (56 mL, 429 mmol) and DIPEA (73.4 mL, 429 mmol) in n-butanol (100 mL) was refluxed (oil bath temp. 140° C.) for 3.5 days. Concentrated in vacuum, partitioned between 25% HCl and TBME, reextracted the organic layer twice with 25% HCl, the aqueous layer was made alkaline with 32% NaOH, extracted with TBME, washed with brine and dried over Na$_2$SO$_4$. Removal of the solvent in vacuum left a brown oil (105.21 g, 104%). Vacuum distillation gave the title compound as a colorless liquid (83.766 g, 83%, 4877-2/2; bp 139-141° C. at 1.4 mbar). MS (ISP) 283.3 [(M+H)$^+$].

Step 2) 3-Trifluoromethyl-pyridin-2-ylamine
CAS-No. [183610-70-0]

To conc. sulfuric acid (230 mL) at 5° C. was dropwise added above (4-methoxy-benzyl)-(3-trifluoromethyl-pyridin-2-yl)-amine (83.76 g, 297 mmol) keeping the internal temperature below 20° C., stirring was continued at 23° C. for 30 min. Poured onto ice, made alkaline with 32% NaOH-sol. (ca. 800 mL) with external ice cooling, saturated with solid NaCl, extracted twice with THF/TBME/DCM, dried over Na$_2$SO$_4$. Removal of the solvent in vacuum left the title compound as a white solid (44.27 g, 92%). MS (ISP) 163.2 [(M+H)$^+$].

Step 3)
5-Bromo-3-trifluoromethyl-pyridin-2-ylamine
CAS-No. [79456-34-1]

To a solution of the above 3-trifluoromethyl-pyridin-2-ylamine (16.21 g, 100 mmol) in acetonitrile (300 mL) at 5° C. was added NBS (17.8 g, 100 mmol) and the mixture was stirred at 23° C. for 1 h. Poured into ice and additional sat. NaHCO$_3$-sol., extracted with EtOAc, washed with brine, dried over Na$_2$SO$_4$. Removal of the solvent in vacuum left a yellow solid, which was filtered through a silica gel and cotton wool column with dichloromethane to give the title compound as a yellow solid (23.71 g, 98%). MS (EI) 240.1 [(M)$^+$], 242.0 [(M+2)$^+$].

Step 4) 3-Trifluoromethyl-5-(4-trifluoromethyl-phenyl)-pyridin-2-ylamine

A mixture of the above 5-bromo-3-trifluoromethyl-pyridin-2-ylamine (9.90 g, 41.1 mmol), commercially available 4-(trifluoromethyl)benzeneboronic acid CAS-No. [128796-39-4] (8.58 g, 45.2 mmol), 1N aqueous $Na_2CO_3$-solution (98.6 mL, 98.6 mmol) and $Pd(PPh_3)_4$ (475 mg, 1 mol %) in DME (205 mL) was refluxed under argon atmosphere for 1 h. Poured into 5% citric acid, extracted with EtOAc, washed the organic layers with sat. $NaHCO_3$-sol. and brine, dried over $Na_2SO_4$. Removal of the solvent in vacuum left a grey solid (13.96 g) which was purified by silica gel flash chromatography with heptane/EtOAc 4:1 to 2:1 to give the title compound as a light yellow solid (10.90 g, 87%). MS (ISN) 305 [(M−H)$^-$]; mp 168° C.

Step 5) N,N-Dimethyl-N'-[3-trifluoromethyl-5-(4-trifluoromethyl-phenyl)-pyridin-2-yl]-formamidine A mixture of the above 3-trifluoromethyl-5-(4-trifluoromethyl-phenyl)-pyridin-2-ylamine (4.59 g, 15 mmol) and dimethylformamide dimethyl acetal (2.25 mL, 16 mmol) in toluene was refluxed for 1 h. The reaction mixture was evaporated and dried at HV to give the title compound as a light yellow solid (4.21 g, 78%). MS (ISP) 362 [(M+H)$^+$]; mp 114° C.

Step 6) 8-Trifluoromethyl-6-(4-trifluoromethyl-phenyl)-imidazo[1,2-a]pyridine-3-carboxylic Acid Ethyl Ester A mixture of the above N,N-dimethyl-N'-[3-trifluoromethyl-5-(4-trifluoromethyl-phenyl)-pyridin-2-yl]-formamidine (3.61 g, 10.0 mmol) and ethyl bromoacetate (3.32 mL, 30.0 mmol) in DMF (10 mL) was stirred at 120° C. for 4 h. Cooled down to 100° C., added DIPEA (0.5 mL, 3.0 mmol) and stirred at 23° C. for 2 h. Poured into sat. $NaHCO_3$-sol., extracted with EtOAc, washed the organic layers with brine, dried over $Na_2SO_4$. Removal of the solvent in vacuum left a brown oil (5.01 g) which was purified by silica gel column chromatography with heptane/EtOAc 9:1 to 4:1 to give the title compound as a light yellow solid (2.89 g, 72%). MS (ISP) 403 [(M+H)$^+$]; mp 132° C.

Step 7) 8-Trifluoromethyl-6-(4-trifluoromethyl-phenyl)-imidazo[1,2-a]pyridine-3-carboxylic Acid To a solution of the above 8-trifluoromethyl-6-(4-trifluoromethyl-phenyl)-imidazo[1,2-a]pyridine-3-carboxylic acid ethyl ester (3.06 g, 7.61 mmol) in THF (45 mL), MeOH (5 mL) and water (11.3 mL) at 23° C. was added $LiOH.H_2O$ (479 mg, 11.41 mmol) and the mixture was stirred at 23° C. for 3 h. Poured into ice water, adjusted pH with 1 N HCl (about 11.41 mL) to pH 2-3, saturated with solid NaCl, extracted with EtOAc, dried over $Na_2SO_4$. Removal of the solvent in vacuum left the title compound as a light brown solid (2.87 g, 101%). MS (ISN) 373 [(M−H)$^-$]; mp 248° C. (dec.).

Example C.33

6-(4-Chloro-phenyl)-8-methyl-imidazo[1,2-a]pyridine-3-carboxylic acid

Step 1) 5-(4-Chloro-phenyl)-3-methyl-pyridin-2-ylamine

Prepared as described in example C.32 (step 4) from commercially available 2-amino-5-bromo-3-methyl-pyridine (4 g, 21.4 mmol) and commercially available 4-chlorophenylboronic acid (3.68 g, 23.5 mmol). Obtained as an off-white solid (3.86 g, 83%). MS (EI) 218.1 [(M)$^+$]; mp 156° C.

Step 2) N'-[5-(4-Chloro-phenyl)-3-methyl-pyridin-2-yl]-N,N-dimethyl-formamidine Prepared as described in example C.32 (step 5) from 5-(4-chloro-phenyl)-3-methyl-pyridin-2-ylamine (4.8 g, 21.9 mmol). Obtained after crystallization from diethyl ether/hexane as an off-white solid (4.73 g, 79%). MS (ISP) 274.0 [(M+H)$^+$]; mp 99° C.

Step 3) 6-(4-Chloro-phenyl)-8-methyl-imidazo[1,2-a]pyridine-3-carboxylic acid ethyl ester Prepared as described in example C.32 (step 6) from N'-[5-(4-chloro-phenyl)-3-methyl-pyridin-2-yl]-N,N-dimethyl-formamidine (4.66 g, 17.0 mmol). Obtained as a light grey solid (5.35 g, 99%). MS (EI) 314.1 [(M)$^+$]; mp 147° C.

Step 4) 6-(4-Chloro-phenyl)-8-methyl-imidazo[1,2-a]pyridine-3-carboxylic acid Prepared as described in example C.32 (step 7) from 6-(4-chloro-phenyl)-8-methyl-imidazo[1,2-a]pyridine-3-carboxylic acid ethyl ester (5.34 g, 17 mmol). Obtained as an off-white solid (3.32 g, 68%). MS (ISN) 285.0 [(M−H)$^-$]; mp 228° C.

Example C.34

8-Methyl-6-(4-trifluoromethyl-phenyl)-imidazo[1,2-a]pyridine-3-carboxylic acid

Step 1) 3-Methyl-5-(4-trifluoromethyl-phenyl)-pyridin-2-ylamine

Prepared as described in example C.32 (step 4) from commercially available 2-amino-5-bromo-3-methyl-pyridine (4.5 g, 24.1 mmol) and commercially available 4-trifluoromethyl-phenylboronic acid (5.03 g, 26.5 mmol). Obtained as an off-white solid (5.36 g, 88%). MS (ISP) 252.9 [(M+H)$^+$]; mp 159° C.

Step 2) N,N-Dimethyl-N'-[3-methyl-5-(4-trifluoromethyl-phenyl)-pyridin-2-yl]-formamidine Prepared as described in example C.32 (step 5) from 3-methyl-5-(4-trifluoromethyl-phenyl)-pyridin-2-ylamine (5.16 g, 20.4 mmol). Obtained as a light yellow solid (6.21 g, 99%). MS (ISP) 308.1 [(M+H)$^+$]; mp 74° C.

Step 3) 8-Methyl-6-(4-trifluoromethyl-phenyl)-imidazo[1,2-a]pyridine-3-carboxylic Acid Ethyl Ester Prepared as described in example C.32 (step 6) from N,N-dimethyl-N'-[3-methyl-5-(4-trifluoromethyl-phenyl)-pyridin-2-yl]-formamidine (5.98 g, 19.5 mmol). Obtained as an off-white solid (5.92 g, 87%). MS (EI) 348.1 [(M)$^+$]; mp 128° C.

Step 4) 8-Methyl-6-(4-trifluoromethyl-phenyl)-imidazo[1,2-a]pyridine-3-carboxylic Acid Prepared as described in example C.32 (step 7) from 8-methyl-6-(4-trifluoromethyl-phenyl)-imidazo[1,2-a]pyridine- 3-carboxylic acid ethyl ester (5.78 g, 16.6 mmol). Obtained as an off-white solid (4.53 g, 85%). MS (ISN) 319.1 [(M−H)⁻]; mp 211° C.

Example C.35

6-(4-Trifluoromethyl-phenyl)-imidazo[1,2-a]pyridine-3-carboxylic acid

Step 1) 5-(4-Trifluoromethyl-phenyl)-pyridin-2-ylamine

Prepared as described in example C.32 (step 4) from commercially available 2-amino-5-bromo-pyridine (3.46 g, 20.0 mmol) and commercially available 4-trifluoromethyl-phenylboronic acid (4.18 g, 22.0 mmol). Obtained as an off-white solid (3.36 g, 71%). Mp 130° C.

Step 2) N,N-Dimethyl-N'-[5-(4-trifluoromethyl-phenyl)-pyridin-2-yl]-formamidine

Prepared as described in example C.32 (step 5) from 5-(4-trifluoromethyl-phenyl)-pyridin-2-ylamine (3.35 g, 14.1 mmol). Obtained as a light brown solid (4.08 g, 99%). MS (ISP) 294.2 [(M+H)⁺]; mp 154° C.

Step 3) 6-(4-Trifluoromethyl-phenyl)-imidazo[1,2-a]pyridine-3-carboxylic Acid Ethyl Ester Prepared as described in example C.32 (step 6) from N,N-dimethyl-N'-[5-(4-trifluoromethyl-phenyl)-pyridin-2-yl]-formamidine (3.93 g, 13.4 mmol). Obtained as a light brown solid (3.07 g, 69%). MS (EI) 334.1 [(M)⁺]; mp 118° C.

Step 4) 6-(4-Trifluoromethyl-phenyl)-imidazo[1,2-a]pyridine-3-carboxylic Acid

Prepared as described in example C.32 (step 7) from 6-(4-trifluoromethyl-phenyl)-imidazo[1,2-a]pyridine-3-carboxylic acid ethyl ester (2.98 g, 8.91 mmol). Obtained as a white solid (2.21 g, 81%). MS (ISN) 305.1 [(M−H)⁻]; mp 220° C.

Example C.36

6-(4-Chloro-phenyl)-imidazo[1,2-a]pyridine-3-carboxylic Acid

Step 1) 5-(4-Chloro-phenyl)-pyridin-2-ylamine

Prepared as described in example C.32 (step 4) from commercially available 2-amino-5-bromo-pyridine (3.46 g, 20.0 mmol) and commercially available 4-chloromethyl-phenylboronic acid (3.44 g, 22.0 mmol). Obtained as a white solid (3.07 g, 75%). MS (EI) 204.0 [(M)⁺]; mp 132° C.

Step 2) N,N-Dimethyl-N'-[5-(4-chloro-phenyl)-pyridin-2-yl]-formamidine

Prepared as described in example C.32 (step 5) from 5-(4-chloro-phenyl)-pyridin-2-ylamine (2.92 g, 14.3 mmol). Obtained as a light brown solid (3.68 g, 99%). MS (ISP) 259.9 [(M+H)⁺]; mp 125° C.

Step 3) 6-(4-Chloro-phenyl)-imidazo[1,2-a]pyridine-3-carboxylic Acid Ethyl Ester Prepared as described in example C.32 (step 6) from N,N-dimethyl-N'-[5-(4-chloro-phenyl)-pyridin-2-yl]-formamidine (3.53 g, 13.6 mmol). Obtained as an off-white solid (3.49 g, 85%). MS (EI) 300.1 [(M)⁺]; mp 130° C.

Step 4) 6-(4-Chloro-phenyl)-imidazo[1,2-a]pyridine-3-carboxylic Acid

Prepared as described in example C.32 (step 7) from 6-(4-chloro-phenyl)-imidazo[1,2-a]pyridine-3-carboxylic acid ethyl ester (3.45 g, 11.5 mmol). Obtained as a white solid (2.69 g, 86%). MS (ISN) 271.2 [(M−H)⁻]; mp 206° C.

Synthesis of Compounds of Formula (I) According to the Invention

Example 1

4-{5-[7-Trifluoromethyl-5-(4-trifluoromethyl-phenyl)-pyrazolo[1,5-a]pyrimidin-3-yl]-[1,2,4]oxadiazol-3-yl}-benzenesulfonamide The title compound was prepared from 7-trifluoromethyl-5-(4-trifluoromethyl-phenyl)-pyrazolo[1,5-a]pyrimidine-3-carboxylic acid (example C.2) (188 mg, 0.5 mmol) and N-hydroxy-4-sulfamoyl-benzamidine [CAS-No. 4476-10-2] (161 mg, 0.75 mmol) according to general procedure II. Obtained after purification by flash chromatography (ethyl acetate/heptane) and crystallization (ethyl acetate/MeOH/hexane) as a light yellow solid (179 mg, 65%). MS (ISN) 552.8 [(M−H)⁻]; mp 275° C.

Example 2

3-{5-[7-Trifluoromethyl-5-(4-trifluoromethyl-phenyl)-pyrazolo[1,5-a]pyrimidin-3-yl]-[1,2,4]oxadiazol-3-yl}-benzenesulfonamide The title compound was prepared from 7-trifluoromethyl-5-(4-trifluoromethyl-phenyl)-pyrazolo[1,5-a]pyrimidine-3-carboxylic acid (example C.2) (188 mg, 0.5 mmol) and N-hydroxy-3-sulfamoyl-benzamidine [CAS-No. 9000-88-7] (161 mg, 0.75 mmol) according to general procedure II. Obtained after purification by column chromatography (dichloromethane/MeOH/NH₄OH) and crystallization (ethyl acetate/MeOH/hexane) as a yellow solid (175 mg, 63%). MS (ISN) 552.8 [(M−H)⁻]; mp 262° C.

Example 3

3-(3-Pyridin-3-yl-[1,2,4]oxadiazol-5-yl)-7-trifluoromethyl-5-(4-trifluoromethyl-phenyl)-pyrazolo[1,5-a]pyrimidine The title compound was prepared from 7-trifluoromethyl-5-(4-trifluoromethyl-phenyl)-pyrazolo[1,5-a]pyrimidine-3-carboxylic acid (example C.2) (188 mg, 0.5 mmol) and commercially available N-hydroxy-nicotinamidine [CAS-No. 1594-58-7] (103 mg, 0.75 mmol) according to general procedure II. Obtained after purification by column chromatography (dichloromethane/MeOH/NH₄OH) and crystallization (dichloromethane/MeOH/hexane) as a yellow solid (126 mg, 53%). MS (EI) 476.1 [(M+H)⁺]; mp 199° C.

Example 4

4-{5-[7-Difluoromethyl-5-(4-trifluoromethyl-phenyl)-pyrazolo[1,5-a]pyrimidin-3-yl]-[1,2,4]oxadiazol-3-yl}-benzenesulfonamide The title compound was prepared from 7-difluoromethyl-5-(4-trifluoromethyl-phenyl)-pyrazolo[1,5-a]pyrimidine-3- carboxylic acid (example C.1) (179 mg, 0.5 mmol) and N-hydroxy-4-sulfamoyl-benzamidine [CAS-No. 4476-10-2] (161 mg, 0.75 mmol) according to general procedure II. Obtained after purification by column chromatography (dichloromethane/MeOH/NH$_4$OH) and crystallization (ethyl acetate/hexane) as a light yellow solid (159 mg, 59%). MS (ISN) 535.3 [(M−H)$^-$]; mp 283° C.

Example 5

3-{5-[7-Difluoromethyl-5-(4-trifluoromethyl-phenyl)-pyrazolo[1,5-a]pyrimidin-3-yl]-[1,2,4]oxadiazol-3-yl}-benzenesulfonamide The title compound was prepared from 7-difluoromethyl-5-(4-trifluoromethyl-phenyl)-pyrazolo[1,5-a]pyrimidine-3-carboxylic acid (example C.1) (179 mg, 0.5 mmol) and N-hydroxy-3-sulfamoyl-benzamidine [CAS-No. 9000-88-7] (161 mg, 0.75 mmol) according to general procedure II. Obtained after purification by column chromatography (dichloromethane/MeOH/NH$_4$OH) and crystallization (ethyl acetate/hexane) as a yellow solid (198 mg, 74%). MS (ISN) 535.3 [(M−H)$^-$]; mp 267° C.

Example 6

3-{5-[5-(4-Chloro-phenyl)-7-cyclopropyl-pyrazolo[1,5-a]pyrimidin-3-yl]-[1,2,4]oxadiazol-3-yl}-benzenesulfonamide The title compound was prepared from 5-(4-chloro-phenyl)-7-cyclopropyl-pyrazolo[1,5-a]pyrimidine-3-carboxylic acid (example C.28) (157 mg, 0.5 mmol) and N-hydroxy-3-sulfamoyl-benzamidine [CAS-No. 9000-88-7] (161 mg, 0.75 mmol) according to general procedure II. Obtained after purification by column chromatography (dichloromethane/MeOH/NH$_4$OH) and crystallization (dichloromethane) as an off-white solid (113 mg, 46%). MS (EI) 492.1 [(M)$^+$]; mp 285° C.

Example 7

3-{5-[7-Cyclopropyl-5-(4-trifluoromethyl-phenyl)-pyrazolo[1,5-a]pyrimidin-3-yl]-[1,2,4]oxadiazol-3-yl}-benzenesulfonamide The title compound was prepared from 7-cyclopropyl-5-(4-trifluoromethyl-phenyl)-pyrazolo[1,5-a]pyrimidine-3-carboxylic acid (example C.29) (174 mg, 0.5 mmol) and N-hydroxy-3-sulfamoyl-benzamidine [CAS-No. 9000-88-7] (161 mg, 0.75 mmol) according to general procedure II. Obtained after purification by column chromatography (dichloromethane/MeOH/NH$_4$OH) and crystallization (ethyl acetate/MeOH/hexane) as an off-white solid (142 mg, 54%). MS (EI) 526.1 [(M)$^+$]; mp 277° C.

Example 8

4-{5-[5-(4-Chloro-phenyl)-7-cyclopropyl-pyrazolo[1,5-a]pyrimidin-3-yl]-[1,2,4]oxadiazol-3-yl}-benzenesulfonamide The title compound was prepared from 5-(4-chloro-phenyl)-7-cyclopropyl-pyrazolo[1,5-a]pyrimidine-3-carboxylic acid (example C.28) (157 mg, 0.5 mmol) and N-hydroxy-4-sulfamoyl-benzamidine [CAS-No. 4476-10-2] (161 mg, 0.75 mmol) according to general procedure II. Obtained after purification by column chromatography (dichloromethane/MeOH/NH$_4$OH) and crystallization (dichloromethane) as a light yellow solid (60 mg, 24%). MS (EI) 492.1 [(M)$^+$]; mp 260° C.

Example 9

4-{5-[7-Cyclopropyl-5-(4-trifluoromethyl-phenyl)-pyrazolo[1,5-a]pyrimidin-3-yl]-[1,2,4]oxadiazol-3-yl}-benzenesulfonamide The title compound was prepared from 7-cyclopropyl-5-(4-trifluoromethyl-phenyl)-pyrazolo[1,5-a]pyrimidine-3-carboxylic acid (example C.29) (174 mg, 0.5 mmol) and N-hydroxy-4-sulfamoyl-benzamidine [CAS-No. 4476-10-2] (161 mg, 0.75 mmol) according to general procedure II. Obtained after purification by column chromatography (dichloromethane/MeOH/NH$_4$OH) and crystallization (dichloromethane/MeOH/hexane) as a light yellow solid (191 mg, 73%). MS (EI) 526.1 [(M)$^+$]; mp 313° C.

Example 10

3-{5-[5-(4-Chloro-phenyl)-7-trifluoromethyl-pyrazolo[1,5-a]pyrimidin-3-yl]-[1,2,4]oxadiazol-3-yl}-benzenesulfonamide The title compound was prepared from 5-(4-chloro-phenyl)-7-trifluoromethyl-pyrazolo[1,5-a]pyrimidine-3-carboxylic acid (example C.4) (171 mg, 0.5 mmol) and N-hydroxy-3-sulfamoyl-benzamidine [CAS-No. 9000-88-7] (161 mg, 0.75 mmol) according to general procedure II. Obtained after purification by column chromatography (dichloromethane/MeOH/NH$_4$OH) and crystallization (dichloromethane) as a light yellow solid (200 mg, 77%). MS (ISP) 521.2 [(M+H)$^+$]; mp 247° C.

Example 11

3-{5-[8-Trifluoromethyl-6-(4-trifluoromethyl-phenyl)-imidazo[1,2-a]pyridin-3-yl]-[1,2,4]oxadiazol-3-yl}-benzenesulfonamide The title compound was prepared from 8-trifluoromethyl-6-(4-trifluoromethyl-phenyl)-imidazo[1,2-a]pyridine-3-carboxylic acid (example C.32) (187 mg, 0.5 mmol) and N-hydroxy-3-sulfamoyl-benzamidine [CAS-No. 9000-88-7] (161 mg, 0.75 mmol) according to general procedure II. Obtained after purification by column chromatography (dichloromethane/MeOH/NH$_4$OH) and crystallization (dichloromethane) as an off-white solid (117 mg, 42%). MS (ISN) 552.0 [(M−H)$^-$]; mp 297° C.

Example 12

4-{5-[5-(4-Chloro-phenyl)-7-trifluoromethyl-pyrazolo[1,5-a]pyrimidin-3-yl]-[1,2,4]oxadiazol-3-yl}-benzenesulfonamide The title compound was prepared from 5-(4-chloro-phenyl)-7-trifluoromethyl-pyrazolo[1,5-a]pyrimidine-3-carboxylic acid (example C.4) (171 mg, 0.5 mmol) and N-hydroxy-4-sulfamoyl-benzamidine [CAS-No. 4476-10-2] (161 mg, 0.75 mmol) according to general procedure II. Obtained after purification by flash chromatography (ethyl acetate/hep-

Example 13

4-{5-[8-Trifluoromethyl-6-(4-trifluoromethyl-phenyl)-imidazo[1,2-a]pyridin-3-yl]-[1,2,4]oxadiazol-3-yl}-benzenesulfonamide The title compound was prepared from 8-trifluoromethyl-6-(4-trifluoromethyl-phenyl)-imidazo[1,2-a]pyridine-3-carboxylic acid (example C.32) (187 mg, 0.5 mmol) and N-hydroxy-4-sulfamoyl-benzamidine [CAS-No. 4476-10-2] (161 mg, 0.75 mmol) according to general procedure II. Obtained after purification by flash chromatography (ethyl acetate/heptane) and crystallization (dichloromethane) as a yellow solid (143 mg, 52%). MS (EI) 553.1 [(M)$^+$]; mp 292° C.

Example 14

4-{3-[7-Trifluoromethyl-5-(4-trifluoromethyl-phenyl)-pyrazolo[1,5-a]pyrimidin-3-yl]-[1,2,4]oxadiazol-5-yl}-benzenesulfonamide The title compound was prepared from N-hydroxy-7-trifluoromethyl-5-(4-trifluoromethyl-phenyl)-pyrazolo[1,5-a]pyrimidine-3-carboxamidine (example B.1) (195 mg, 0.5 mmol) and commercially available 4-sulfamoyl-benzoic acid (101 mg, 0.5 mmol) according to general procedure II. Obtained after purification by flash chromatography (ethyl acetate/heptane) and crystallization (dichloromethane) as a yellow solid (155 mg, 56%). MS (ISN) 553.3 [(M−H)$^−$]; mp 292° C.

Example 15

3-{3-[7-Trifluoromethyl-5-(4-trifluoromethyl-phenyl)-pyrazolo[1,5-a]pyrimidin-3-yl]-[1,2,4]oxadiazol-5-yl}-benzenesulfonamide The title compound was prepared from N-hydroxy-7-trifluoromethyl-5-(4-trifluoromethyl-phenyl)-pyrazolo[1,5-a]pyrimidine-3-carboxamidine (example B.1) (195 mg, 0.5 mmol) and commercially available 3-sulfamoyl-benzoic acid (101 mg, 0.5 mmol) according to general procedure II. Obtained after purification by flash chromatography (ethyl acetate/heptane) and crystallization (dichloromethane) as a yellow solid (144 mg, 52%). MS (ISN) 553.3 [(M−H)$^−$]; mp 285° C.

Example 16

3-(5-{5-[3-(2,2,2-Trifluoro-ethoxy)-4-trifluoromethyl-phenyl]-7-trifluoromethyl-pyrazolo[1,5-a]pyrimidin-3-yl}-[1,2,4]oxadiazol-3-yl)-benzenesulfonamide The title compound was prepared from 5-[3-(2,2,2-trifluoro-ethoxy)-4-trifluoromethyl-phenyl]-7-trifluoromethyl-pyrazolo[1,5-a]pyrimidine-3-carboxylic acid (example C.10) (237 mg, 0.5 mmol) and N-hydroxy-3-sulfamoyl-benzamidine [CAS-No. 9000-88-7] (161 mg, 0.75 mmol) according to general procedure II. Obtained after purification by flash chromatography (ethyl acetate/hexane) and crystallization (dichloromethane) as a light yellow solid (220 mg, 67%). MS (EI) 652.2 [(M)$^+$]; mp 250° C.

Example 17

3-{5-[5-(3-Methyl-4-trifluoromethyl-phenyl)-7-trifluoromethyl-pyrazolo[1,5-a]pyrimidin-3-yl]-[1,2,4]oxadiazol-3-yl}-benzenesulfonamide The title compound was prepared from 5-(3-methyl-4-trifluoromethyl-phenyl)-7-trifluoromethyl-pyrazolo[1,5-a]pyrimidine-3-carboxylic acid (example C.8) (195 mg, 0.5 mmol) and N-hydroxy-3-sulfamoyl-benzamidine [CAS-No. 9000-88-7] (161 mg, 0.75 mmol) according to general procedure II. Obtained after purification by flash chromatography (ethyl acetate/heptane) and crystallization (dichloromethane) as a light yellow solid (190 mg, 67%). MS (EI) 568.1 [(M)$^+$]; mp 270° C.

Example 18

4-{5-[5-(3-Methyl-4-trifluoromethyl-phenyl)-7-trifluoromethyl-pyrazolo[1,5-a]pyrimidin-3-yl]-[1,2,4]oxadiazol-3-yl}-benzenesulfonamide The title compound was prepared from 5-(3-methyl-4-trifluoromethyl-phenyl)-7-trifluoromethyl-pyrazolo[1,5-a]pyrimidine-3-carboxylic acid (example C.8) (195 mg, 0.5 mmol) and N-hydroxy-4-sulfamoyl-benzamidine [CAS-No. 4476-10-2] (161 mg, 0.75 mmol) according to general procedure II. Obtained after purification by flash chromatography (ethyl acetate/heptane) and crystallization (dichloromethane) as a yellow solid (200 mg, 70%). MS (ISN) 567.2 [(M−H)$^−$]; mp 273° C.

Example 19

3-{5-[5-(4-Chloro-phenyl)-7-difluoromethyl-pyrazolo[1,5-a]pyrimidin-3-yl]-[1,2,4]oxadiazol-3-yl}-benzenesulfonamide The title compound was prepared from 5-(4-chloro-phenyl)-7-difluoromethyl-pyrazolo[1,5-a]pyrimidine-3-carboxylic acid (example C.3) (162 mg, 0.5 mmol) and N-hydroxy-3-sulfamoyl-benzamidine [CAS-No. 9000-88-7] (161 mg, 0.75 mmol) according to general procedure II. Obtained after trituration with water and further purification by crystallization (dichloromethane) as a light yellow solid (170 mg, 68%). MS (ISN) 501.1 [(M−H)$^−$]; mp 231° C.

Example 20

5-{5-[5-(4-Chloro-phenyl)-7-cyclopropyl-pyrazolo[1,5-a]pyrimidin-3-yl]-[1,2,4]oxadiazol-3-yl}-thiophene-2-sulfonic acid amide The title compound was prepared from 5-(4-chloro-phenyl)-7-cyclopropyl-pyrazolo[1,5-a]pyrimidine-3-carboxylic acid (example C.28) (157 mg, 0.5 mmol) and N-hydroxy-5-sulfamoyl-thiophene-2-carboxamidine (example B.2) (166 mg, 0.75 mmol) according to general procedure II. Obtained after purification by flash chromatography (ethyl acetate/heptane) and crystallization (ethyl acetate/dichloromethane) as a light brown solid (130 mg, 52%). MS (EI) 498.1 [(M)$^+$]; mp 294° C.

Example 21

4-{3-[4-Trifluoromethyl-2-(4-trifluoromethyl-phenyl)-imidazo[1,5-a]pyrimidin-8-yl]-[1,2,4]oxadiazol-5-yl}-benzenesulfonamide The title compound was prepared from N-hydroxy-4-trifluoromethyl-2-(4-trifluoromethyl-phenyl)-imidazo[1,5-a]pyrimidine-8-carboxamidine (example B.3) (195 mg, 0.5 mmol) and commercially available 4-sulfamoyl-benzoic acid (101 mg, 0.5 mmol) according to general procedure II. Obtained after purification by column chromatography (dichloromethane/MeOH/NH$_4$OH) and crystallization (dichloromethane) as a yellow solid (61 mg, 22%). MS (ISP) 555.3 [(M+H)$^+$]; mp 303° C.

Example 22

5-{5-[5-(3-Methyl-4-trifluoromethyl-phenyl)-7-trifluoromethyl-pyrazolo[1,5-a]pyrimidin-3-yl]-[1,2,4]oxadiazol-3-yl}-thiophene-2-sulfonic acid amide The title compound was prepared from 5-(3-methyl-4-trifluoromethyl-phenyl)-7-trifluoromethyl-pyrazolo[1,5-a]pyrimidine-3-carboxylic acid (example C.8) (195 mg, 0.5 mmol) and N-hydroxy-5-sulfamoyl-thiophene-2-carboxamidine (example B.2) (166 mg, 0.75 mmol) according to general procedure II. Obtained after purification by flash chromatography (ethyl acetate/heptane) and crystallization (dichloromethane) as a light yellow solid (50 mg, 17%). MS (ISN) 573.2 [(M−H)$^−$]; mp 324° C.

Example 23

5-(5-{5-[3-(2,2,2-Trifluoro-ethoxy)-4-trifluoromethyl-phenyl]-7-trifluoromethyl-pyrazolo[1,5-a]pyrimidin-3-yl}-[1,2,4]oxadiazol-3-yl)-thiophene-2-sulfonic Acid Amide The title compound was prepared from 5-[3-(2,2,2-trifluoro-ethoxy)-4-trifluoromethyl-phenyl]-7-trifluoromethyl-pyrazolo[1,5-a]pyrimidine-3-carboxylic acid (example C.10) (237 mg, 0.5 mmol) and N-hydroxy-5-sulfamoyl-thiophene-2-carboxamidine (example B.2) (166 mg, 0.75 mmol) according to general procedure II. Obtained after purification by flash chromatography (ethyl acetate/hexane) and crystallization (dichloromethane) as a yellow solid (220 mg, 67%). MS (ISP) 659.3 [(M+H)$^+$]; mp 255° C.

Example 24

5-{5-[7-Cyclopropyl-5-(4-trifluoromethyl-phenyl)-pyrazolo[1,5-a]pyrimidin-3-yl]-[1,2,4]oxadiazol-3-yl}-thiophene-2-sulfonic Acid Amide The title compound was prepared from 7-cyclopropyl-5-(4-trifluoromethyl-phenyl)-pyrazolo[1,5-a]pyrimidine-3-carboxylic acid (example C.29) (174 mg, 0.5 mmol) N-hydroxy-5-sulfamoyl-thiophene-2-carboxamidine (example B.2) (166 mg, 0.75 mmol) and according to general procedure II. Obtained after purification by flash chromatography (ethyl acetate/heptane) and crystallization (dichloromethane/ethyl acetate) as a yellow solid (180 mg, 68%). MS (ISP) 533.3 [(M+H)$^+$]; mp 290° C.

Example 25

4-{5-[7-Trifluoromethyl-5-(3-trifluoromethyl-phenyl)-pyrazolo[1,5-a]pyrimidin-3-yl]-[1,2,4]oxadiazol-3-yl}-benzenesulfonamide The title compound was prepared from 7-trifluoromethyl-5-(3-trifluoromethyl-phenyl)-pyrazolo[1,5-a]pyrimidine-3-carboxylic acid (example C.31) (188 mg, 0.5 mmol) and N-hydroxy-4-sulfamoyl-benzamidine [CAS-No. 4476-10-2] (161 mg, 0.75 mmol) according to general procedure II. Obtained after purification by flash chromatography (ethyl acetate/heptane) and crystallization (ethyl acetate/dichloromethane) as a yellow solid (220 mg, 79%). MS (ISP) 555.3 [(M+H)$^+$]; mp 300° C.

Example 26

3-{5-[7-Trifluoromethyl-5-(3-trifluoromethyl-phenyl)-pyrazolo[1,5-a]pyrimidin-3-yl]-[1,2,4]oxadiazol-3-yl}-benzenesulfonamide The title compound was prepared from 7-trifluoromethyl-5-(3-trifluoromethyl-phenyl)-pyrazolo[1,5-a]pyrimidine-3-carboxylic acid (example C.31) (188 mg, 0.5 mmol) and N-hydroxy-3-sulfamoyl-benzamidine [CAS-No. 9000-88-7] (161 mg, 0.75 mmol) according to general procedure II. Obtained after purification by flash chromatography (ethyl acetate/heptane) and crystallization (dichloromethane) as a light yellow solid (120 mg, 43%). MS (ISN) 552.9 [(M−H)$^−$]; mp 251° C.

Example 27

5-{5-[7-Trifluoromethyl-5-(4-trifluoromethyl-phenyl)-pyrazolo[1,5-a]pyrimidin-3-yl]-[1,2,4]oxadiazol-3-yl}-thiophene-2-sulfonic Acid Amide The title compound was prepared from 7-trifluoromethyl-5-(4-trifluoromethyl-phenyl)-pyrazolo[1,5-a]pyrimidine-3-carboxylic acid (example C.2) (188 mg, 0.5 mmol) and N-hydroxy-5-sulfamoyl-thiophene-2-carboxamidine (example B.2) (166 mg, 0.75 mmol) according to general procedure II. Obtained after purification by flash chromatography (ethyl acetate/heptane) and crystallization (dichloromethane) as an off-white solid (130 mg, 46%). MS (ISN) 558.0 [(M−H)$^−$]; mp 276° C.

Example 28

5-{5-[5-(4-Chloro-phenyl)-7-trifluoromethyl-pyrazolo[1,5-a]pyrimidin-3-yl]-[1,2,4]oxadiazol-3-yl}-thiophene-2-sulfonic Acid Amide The title compound was prepared from 5-(4-chloro-phenyl)-7-trifluoromethyl-pyrazolo[1,5-a]pyrimidine-3-carboxylic acid (example C.4) (171 mg, 0.5 mmol) and N-hydroxy-5-sulfamoyl-thiophene-2-carboxamidine (example B.2) (166 mg, 0.75 mmol) according to general procedure II. Obtained after purification by flash chromatography (ethyl acetate/heptane) and crystallization (dichloromethane) as a yellow solid (180 mg, 68%). MS (ISN) 525.0 [(M−H)$^−$]; mp 294° C.

Example 29

5-{5-[5-(4-Chloro-phenyl)-7-difluoromethyl-pyrazolo[1,5-a]pyrimidin-3-yl]-[1,2,4]oxadiazol-3-yl}-thiophene-2-sulfonic Acid Amide The title compound was prepared from 5-(4-chloro-phenyl)-7-difluoromethyl-pyrazolo[1,5-a]pyrimidine-3-carboxylic acid (example C.3) (162 mg, 0.5 mmol) and N-hydroxy-5-sulfamoyl-thiophene-2-carboxamidine (example B.2) (166 mg, 0.75 mmol) according to general procedure II. Obtained after purification by flash chromatography (ethyl acetate/heptane) and crystallization (dichloromethane) as a light yellow solid (96 mg, 38%). MS (EI) 508.0 [(M)$^+$]; mp 259° C.

Example 30

5-{5-[7-Methyl-5-(4-trifluoromethyl-phenyl)-pyrazolo[1,5-a]pyrimidin-3-yl]-[1,2,4]oxadiazol-3-yl}-thiophene-2-sulfonic Acid Amide The title compound was prepared from 7-methyl-5-(4-trifluoromethyl-phenyl)-pyrazolo[1,5-a]pyrimidine-3-carboxylic acid (example C.25) (161 mg, 0.5 mmol) and N-hydroxy-5-sulfamoyl-thiophene-2-carboxamidine (example B.2) (166 mg, 0.75 mmol) according to general procedure II. Obtained after purification by column chromatography (dichloromethane/MeOH/NH$_4$OH) and crystallization (dichloromethane/MeOH) as a light yellow solid (88 mg, 35%). MS (EI) 506.1 [(M+H)$^+$]; mp 276° C.

Example 31

5-{5-[7-Difluoromethyl-5-(4-trifluoromethyl-phenyl)-pyrazolo[1,5-a]pyrimidin-3-yl]-[1,2,4]oxadiazol-3-yl}-thiophene-2-sulfonic Acid Amide The title compound was prepared from 7-difluoromethyl-5-(4-trifluoromethyl-phenyl)-pyrazolo[1,5-a]pyrimidine-3-carboxylic acid (example C.1) (179 mg, 0.5 mmol) and N-hydroxy-5-sulfamoyl-thiophene-2-carboxamidine (example B.2) (166 mg, 0.75 mmol) according to general procedure II. Obtained after purification by flash chromatography (ethyl acetate/heptane) and crystallization (dichloromethane) as a yellow solid (200 mg, 74%). MS (EI) 542.0 [(M+H)$^+$]; mp 278° C.

Example 32

5-{5-[5-(4-Chloro-phenyl)-7-methyl-pyrazolo[1,5-a]pyrimidin-3-yl]-[1,2,4]oxadiazol-3-yl}-thiophene-2-sulfonic Acid Amide The title compound was prepared from 5-(4-chloro-phenyl)-7-methyl-pyrazolo[1,5-a]pyrimidine-3-carboxylic acid (example C.24) (144 mg, 0.5 mmol) and N-hydroxy-5-sulfamoyl-thiophene-2-carboxamidine (example B.2) (166 mg, 0.75 mmol) according to general procedure II. Obtained after purification by column chromatography (dichloromethane/MeOH/NH$_4$OH)) and crystallization (MeOH/dichloromethane) as a light yellow solid (79 mg, 33%). MS (ISP) 473.3 [(M+H)$^+$]; mp 253° C.

Example 33

5-{3-[7-Trifluoromethyl-5-(4-trifluoromethyl-phenyl)-pyrazolo[1,5-a]pyrimidin-3-yl]-[1,2,4]oxadiazol-5-yl}-thiophene-2-sulfonic Acid Amide The title compound was prepared from N-hydroxy-4-trifluoromethyl-2-(4-trifluoromethyl-phenyl)-imidazo[1,5-a]pyrimidine-8-carboxamidine (example B.3) (195 mg, 0.5 mmol) and commercially available 2-sulfamoyl-thiophene-5-carboxylic acid [CAS-No. 7353-87-9] (104 mg, 0.5 mmol) according to general procedure II. Obtained after purification by flash chromatography (ethyl acetate/heptane) and crystallization (dichloromethane) as a yellow solid (110 mg, 39%). MS (EI) 560.0 [(M)$^+$]; mp 272° C.

Example 34

5-{5-[7-Trifluoromethyl-5-(3-trifluoromethyl-phenyl)-pyrazolo[1,5-a]pyrimidin-3-yl]-[1,2,4]oxadiazol-3-yl}-pyridin-2-ylamine The title compound was prepared from 7-trifluoromethyl-5-(3-trifluoromethyl-phenyl)-pyrazolo[1,5-a]pyrimidine-3-carboxylic acid (example C.31) (188 mg, 0.5 mmol) and 6-amino-N-hydroxy-nicotinamidine (example B.4) (114 mg, 0.75 mmol) according to general procedure II. Obtained after purification by flash chromatography (ethyl acetate/heptane) and crystallization (dichloromethane/hexane) as a yellow solid (22 mg, 9%). MS (ISP) 492.1 [(M+H)$^+$]; mp 264° C.

Example 35

5-{5-[7-Trifluoromethyl-5-(4-trifluoromethyl-phenyl)-pyrazolo[1,5-a]pyrimidin-3-yl]-[1,2,4]oxadiazol-3-yl}-pyridin-2-ylamine The title compound was prepared from 7-trifluoromethyl-5-(4-trifluoromethyl-phenyl)-pyrazolo[1,5-a]pyrimidine-3-carboxylic acid (example C.2) (188 mg, 0.5 mmol) and 6-amino-N-hydroxy-nicotinamidine (example B.4) (114 mg, 0.75 mmol) according to general procedure II. Obtained after purification by flash chromatography (ethyl acetate/heptane) and crystallization (dichloromethane/hexane) as a yellow solid (85 mg, 35%). MS (ISP) 492.1 [(M+H)$^+$]; mp 257° C.

Example 36

5-{5-[7-Difluoromethyl-5-(4-trifluoromethyl-phenyl)-pyrazolo[1,5-a]pyrimidin-3-yl]-[1,2,4]oxadiazol-3-yl}-pyridin-2-ylamine The title compound was prepared from 7-difluoromethyl-5-(4-trifluoromethyl-phenyl)-pyrazolo[1,5-a]pyrimidine-3-carboxylic acid (example C.1) (179 mg, 0.5 mmol) and 6-amino-N-hydroxy-nicotinamidine (example B.4) (114 mg, 0.75 mmol) according to general procedure II. Obtained after purification by flash chromatography (ethyl acetate/heptane) and crystallization (ethyl acetate/hexane) as a yellow solid (84 mg, 35%). MS (ISP) 474.0 [(M+H)$^+$]; mp 242° C.

Example 37

5-{5-[5-(3-Methyl-4-trifluoromethyl-phenyl)-7-trifluoromethyl-pyrazolo[1,5-a]pyrimidin-3-yl]-[1,2,4]oxadiazol-3-yl}-pyridin-2-ylamine The title compound was prepared from 5-(3-methyl-4-trifluoromethyl-phenyl)-7-trifluoromethyl-pyrazolo[1,5-a]pyrimidine-3-carboxylic acid (example C.8) (195 mg, 0.5 mmol) and 6-amino-N-hydroxy-nicotinamidine (example B.4) (114 mg, 0.75 mmol) according to general procedure II. Obtained after purification by flash chromatography (ethyl acetate/heptane) and crystallization (dichloromethane/hexane) as a yellow solid (98 mg, 39%). MS (ISP) 506.2 [(M+H)$^+$]; mp 220° C.

Example 38

3-{5-[5-(4-Chloro-phenyl)-7-methyl-pyrazolo[1,5-a]pyrimidin-3-yl]-[1,2,4]oxadiazol-3-yl}-benzenesulfonamide The title compound was prepared from 5-(4-chloro-phenyl)-7-methyl-pyrazolo[1,5-a]pyrimidine-3-carboxylic acid (example C.24) (144 mg, 0.5 mmol) and N-hydroxy-3-sulfamoyl-benzamidine [CAS-No. 9000-88-7] (161 mg, 0.75 mmol) according to general procedure II. Obtained after purification by flash chromatography (ethyl acetate/heptane) and crystallization (MeOH/dichloromethane) as a light yellow solid (70 mg, 30%). MS (EI) 466.1 [(M)$^+$]; mp 275° C.

Example 39

4-{5-[6-(4-Chloro-phenyl)-8-methyl-imidazo[1,2-a]pyridin-3-yl]-[1,2,4]oxadiazol-3-yl}-benzenesulfonamide The title compound was prepared from 6-(4-chloro-phenyl)-8-methyl-imidazo[1,2-a]pyridine-3-carboxylic acid (example C.33) (143 mg, 0.5 mmol) and N-hydroxy-4-sulfamoyl-benzamidine [CAS-No. 4476-10-2] (161 mg, 0.75 mmol) according to general procedure II. Obtained after purification by flash chromatography (ethyl acetate/heptane) and crystallization (MeOH) as an off-white solid (143 mg, 61%). MS (EI) 465.1 [(M)$^+$]; mp 311° C.

Example 40

3-{5-[6-(4-Chloro-phenyl)-8-methyl-imidazo[1,2-a]pyridin-3-yl]-[1,2,4]oxadiazol-3-yl}-benzenesulfonamide The title compound was prepared from 6-(4-chloro-phenyl)-8-methyl-imidazo[1,2-a]pyridine-3-carboxylic acid (example C.33) (143 mg, 0.5 mmol) and N-hydroxy-3-sulfamoyl-benzamidine [CAS-No. 9000-88-7] (161 mg, 0.75 mmol) according to general procedure II. Obtained after trituration with water and further purification by crystallization (MeOH/diethyl ether) as an off-white solid (152 mg, 65%). MS (EI) 465.1 [(M)$^+$]; mp 301° C.

Example 41

5-{5-[6-(4-Chloro-phenyl)-8-methyl-imidazo[1,2-a]pyridin-3-yl]-[1,2,4]oxadiazol-3-yl}-thiophene-2-sulfonic Acid Amide The title compound was prepared from 6-(4-chloro-phenyl)-8-methyl-imidazo[1,2-a]pyridine-3-carboxylic acid (example C.33) (143 mg, 0.5 mmol) and N-hydroxy-5-sulfamoyl-thiophene-2-carboxamidine (example B.2) (166 mg, 0.75 mmol) according to general procedure II. Obtained after trituration with water and further purification by crystallization (MeOH/diethyl ether) as an off-white solid (159 mg, 67%). MS (ISN) 470.0 [(M−H)$^-$]; mp 271° C.

Example 42

5-{5-[4-Trifluoromethyl-2-(4-trifluoromethyl-phenyl)-imidazo[1,5-a]pyrimidin-8-yl]-[1,2,4]oxadiazol-3-yl}-thiophene-2-sulfonic Acid Amide The title compound was prepared from 4-trifluoromethyl-2-(4-trifluoromethyl-phenyl)-imidazo[1,5-a]pyrimidine-8-carboxylic acid (example C.30) (188 mg, 0.5 mmol) and N-hydroxy-5-sulfamoyl-thiophene-2-carboxamidine (example B.2) (166 mg, 0.75 mmol) according to general procedure II. Obtained after purification by flash chromatography (ethyl acetate/heptane) and crystallization (dichloromethane/ethyl acetate) as a yellow solid (199 mg, 71%). MS (ISN) 559.1 [(M−H)$^-$]; mp 295° C.

Example 43

4-{5-[8-Methyl-6-(4-trifluoromethyl-phenyl)-imidazo[1,2-a]pyridin-3-yl]-[1,2,4]oxadiazol-3-yl}-benzenesulfonamide The title compound was prepared from 8-methyl-6-(4-trifluoromethyl-phenyl)-imidazo[1,2-a]pyridine-3-carboxylic acid (example C.34) (160 mg, 0.5 mmol) and N-hydroxy-4-sulfamoyl-benzamidine [CAS-No. 4476-10-2] (161 mg, 0.75 mmol) according to general procedure II. Obtained after trituration with water and further purification by crystallization (MeOH/diethyl ether) as an off-white solid (146 mg, 58%). MS (ISP) 500.3 [(M+H)$^+$]; mp 290° C.

Example 44

3-{5-[8-Methyl-6-(4-trifluoromethyl-phenyl)-imidazo[1,2-a]pyridin-3-yl]-[1,2,4]oxadiazol-3-yl}-benzenesulfonamide The title compound was prepared from 8-methyl-6-(4-trifluoromethyl-phenyl)-imidazo[1,2-a]pyridine-3-carboxylic acid (example C.34) (160 mg, 0.5 mmol) and N-hydroxy-3-sulfamoyl-benzamidine [CAS-No. 9000-88-7] (161 mg, 0.75 mmol) according to general procedure II. Obtained after trituration with water and further purification by crystallization (MeOH/diethyl ether) as an off-white solid (175 mg, 70%). MS (ISP) 500.3 [(M+H)$^+$]; mp 326° C.

Example 45

5-{5-[8-Methyl-6-(4-trifluoromethyl-phenyl)-imidazo[1,2-a]pyridin-3-yl]-[1,2,4]oxadiazol-3-yl}-thiophene-2-sulfonic Acid Amide The title compound was prepared from 8-methyl-6-(4-trifluoromethyl-phenyl)-imidazo[1,2-a]pyridine-3-carboxylic acid (example C.34) (160 mg, 0.5 mmol) and N-hydroxy-5-sulfamoyl-thiophene-2-carboxamidine (example B.2) (166 mg, 0.75 mmol) according to general procedure II. Obtained after purification by column chromatography (dichloromethane/MeOH/NH$_4$OH) and crystallization (diethyl ether/MeOH) as a pink solid (147 mg, 58%). MS (EI) 505.1 [(M)$^+$]; mp 285° C.

Example 46

5-{5-[7-Trifluoromethyl-5-(4-trifluoromethyl-phenyl)-pyrazolo[1,5-a]pyrimidin-3-yl]-[1,2,4]oxadiazol-3-yl}-pyrimidin-2-ylamine The title compound was prepared from 7-trifluoromethyl-5-(4-trifluoromethyl-phenyl)-pyrazolo[1,5-a]pyrimidine-3-carboxylic acid (example C.2) (188 mg, 0.5 mmol) 2-amino-N-hydroxy-pyrimidine-5-carboxamidine (example B.5) (115 mg, 0.75 mmol) according to general procedure II. Obtained after purification by flash chromatography (ethyl acetate/heptane) and crystallization (dichloromethane/MeOH) as a yellow solid (160 mg, 65%). MS (ISP) 493.3 [(M+H)$^+$]; mp 254° C.

Example 47

5-{5-[8-Methyl-6-(4-trifluoromethyl-phenyl)-imidazo[1,2-a]pyridin-3-yl]-[1,2,4]oxadiazol-3-yl}-pyridin-2-ylamine The title compound was prepared from 8-methyl-6-(4-trifluoromethyl-phenyl)-imidazo[1,2-a]pyridine-3-carboxylic acid (example C.34) (160 mg, 0.5 mmol) and 6-amino-N-hydroxy-nicotinamidine (example B.4) (114 mg, 0.75 mmol) according to general procedure II. Obtained after purification by column chromatography (dichloromethane/MeOH/NH$_4$OH) and crystallization (diethyl ether) as a white solid (32 mg, 15%). MS (EI) 436.1 [(M)$^+$]; mp 257° C.

Example 48

5-{5-[8-Methyl-6-(4-trifluoromethyl-phenyl)-imidazo[1,2-a]pyridin-3-yl]-[1,2,4]oxadiazol-3-yl}-pyrimidin-2-ylamine The title compound was prepared from 8-methyl-6-(4-trifluoromethyl-phenyl)-imidazo[1,2-a]pyridine-3-carboxylic acid (example C.34) (160 mg, 0.5 mmol) 2-amino-N-hydroxy-pyrimidine-5-carboxamidine (example B.5) (115 mg, 0.75 mmol) according to general procedure II. Obtained after purification by flash chromatography (ethyl acetate/heptane) and crystallization (dichloromethane/hexane) as a white solid (60 mg, 27%). MS (ISP) 438.3 [(M+H)$^+$]; mp 302° C.

Example 49

3-{5-[5-(4-Chloro-phenyl)-pyrazolo[1,5-a]pyrimidin-3-yl]-[1,2,4]oxadiazol-3-yl}-benzenesulfonamide The title compound was prepared from 5-(4-chloro-phenyl)-pyrazolo[1,5-a]pyrimidine-3-carboxylic acid (example C.22) (137 mg, 0.5 mmol) and N-hydroxy-3-sulfamoyl-benzamidine [CAS-No. 9000-88-7] (161 mg, 0.75 mmol) according to general procedure II. Obtained after purification by flash chromatography (dichloromethane/MeOH) and crystallization (dichloromethane) as an off-white solid (86 mg, 38%). MS (ISN) 451.2 [(M−H)$^−$]; mp 223° C.

Example 50

4-{5-[6-(4-Trifluoromethyl-phenyl)-imidazo[1,2-a]pyridin-3-yl]-[1,2,4]oxadiazol-3-yl}-benzenesulfonamide The title compound was prepared from 6-(4-trifluoromethyl-phenyl)-imidazo[1,2-a]pyridine-3-carboxylic acid (example C.35) (153 mg, 0.5 mmol) and N-hydroxy-4-sulfamoyl-benzamidine [CAS-No. 4476-10-2] (161 mg, 0.75 mmol) according to general procedure II. Obtained after trituration with water and further purification by crystallization (heptane/diethyl ether) as an off-white solid (186 mg, 77%). MS (ISP) 486.3 [(M+H)$^+$]; mp 288° C.

Example 51

3-{5-[6-(4-Trifluoromethyl-phenyl)-imidazo[1,2-a]pyridin-3-yl]-[1,2,4]oxadiazol-3-yl}-benzenesulfonamide The title compound was prepared from 6-(4-trifluoromethyl-phenyl)-imidazo[1,2-a]pyridine-3-carboxylic acid (example C.35) (153 mg, 0.5 mmol) and N-hydroxy-3-sulfamoyl-benzamidine [CAS-No. 9000-88-7] (161 mg, 0.75 mmol) according to general procedure II. Obtained after trituration with water and further purification by crystallization (MeOH/diethyl ether) as an off-white solid (202 mg, 83%). MS (ISP) 486.3 [(M+H)$^+$]; mp 288° C.

Example 52

5-{5-[5-(4-Trifluoromethyl-phenyl)-pyrazolo[1,5-a]pyrimidin-3-yl]-[1,2,4]oxadiazol-3-yl}-thiophene-2-sulfonic Acid Amide The title compound was prepared from 6-(4-trifluoromethyl-phenyl)-imidazo[1,2-a]pyridine-3-carboxylic acid (example C.23) (154 mg, 0.5 mmol) and N-hydroxy-5-sulfamoyl-thiophene-2-carboxamidine (example B.2) (166 mg, 0.75 mmol) according to general procedure II. Obtained after purification by flash chromatography (dichloromethane/MeOH) and crystallization (dichloromethane) as a yellow solid (154 mg, 62%). MS (ISP) 493.0 [(M+H)$^+$]; mp 251° C.

Example 53

3-{5-[5-(4-Trifluoromethyl-phenyl)-pyrazolo[1,5-a]pyrimidin-3-yl]-[1,2,4]oxadiazol-3-yl}-benzenesulfonamide The title compound was prepared from 6-(4-trifluoromethyl-phenyl)-imidazo[1,2-a]pyridine-3-carboxylic acid (example C.23) (154 mg, 0.5 mmol) and N-hydroxy-3-sulfamoyl-benzamidine [CAS-No. 9000-88-7] (161 mg, 0.75 mmol) according to general procedure II. Obtained after purification by flash chromatography (dichloromethane/MeOH) and crystallization (dichloromethane) as a yellow solid (96 mg, 39%). MS (ISP) 487.1 [(M+H)$^+$]; mp 270° C.

Example 54

5-{5-[6-(4-Trifluoromethyl-phenyl)-imidazo[1,2-a]pyridin-3-yl]-[1,2,4]oxadiazol-3-yl}-thiophene-2-sulfonic acid amide The title compound was prepared from 6-(4-trifluoromethyl-phenyl)-imidazo[1,2-a]pyridine-3-carboxylic acid (example C.35) (153 mg, 0.5 mmol) and N-hydroxy-5-sulfamoyl-thiophene-2-carboxamidine (example B.2) (166 mg, 0.75 mmol) according to general procedure II. Obtained after trituration with water and further purification by crystallization (heptane/diethyl ether) as an off-white solid (179 mg, 83%). MS (ISP) 492.2 [(M+H)$^+$]; mp 280° C.

Example 55

5-{5-[6-(4-Chloro-phenyl)-imidazo[1,2-a]pyridin-3-yl]-[1,2,4]oxadiazol-3-yl}-thiophene-2-sulfonic Acid Amide The title compound was prepared from 6-(4-chloro-phenyl)-imidazo[1,2-a]pyridine-3-carboxylic acid (example C.36) (136 mg, 0.5 mmol) and N-hydroxy-5-sulfamoyl-thiophene-2-carboxamidine (example B.2) (166 mg, 0.75 mmol) according to general procedure II. Obtained after trituration with water and further purification by crystallization (heptane/diethyl ether) as an off-white solid (160 mg, 70%). MS (ISP) 458.2 [(M+H)$^+$]; mp 263° C.

Example 56

5-{5-[6-(4-Trifluoromethyl-phenyl)-imidazo[1,2-a]pyridin-3-yl]-[1,2,4]oxadiazol-3-yl}-pyridin-2-ylamine The title compound was prepared from 6-(4-trifluoromethyl-phenyl)-imidazo[1,2-a]pyridine-3-carboxylic acid (example C.35) (153 mg, 0.5 mmol) and 6-amino-N-hydroxy-nicotinamidine (example B.4) (114 mg, 0.75 mmol) according to general procedure II. Obtained after flash chromatography on silica gel (ethyl acetate) and further purification by crystallization (MeOH/diethyl ether) as a white solid (27 mg, 13%). MS (ISP) 423.3 [(M+H)$^+$]; mp 258° C.

Example 57

5-{5-[6-(4-Chloro-phenyl)-imidazo[1,2-a]pyridin-3-yl]-[1,2,4]oxadiazol-3-yl}-pyridin-2-ylamine The title compound was prepared from 6-(4-chloro-phenyl)-imidazo[1,2-a]pyridine-3-carboxylic acid (example C.36) (136 mg, 0.5 mmol) and 6-amino-N-hydroxy-nicotinamidine (example B.4) (114 mg, 0.75 mmol) according to general procedure II. Obtained after flash chromatography on silica gel (ethyl acetate) and further purification by crystallization (MeOH/diethyl ether) as a white solid (34 mg, 17%). MS (ISP) 389.3 [(M+H)$^+$]; mp 273° C.

Example 58

4-{5-[7-Trifluoromethyl-5-(4-trifluoromethyl-phenyl)-pyrazolo[1,5-a]pyrimidin-3-yl]-[1,2,4]oxadiazol-3-yl}-pyridin-2-ylamine The title compound was prepared from 7-trifluoromethyl-5-(4-trifluoromethyl-phenyl)-pyrazolo[1,5-a]pyrimidine-3-carboxylic acid (example C.2) (188 mg, 0.5 mmol) and 2-amino-N-hydroxy-pyridine-4-carboxamidine (example B.6) (114 mg, 0.75 mmol) according to general procedure II. Obtained after purification by flash chromatography on silica gel (ethyl acetate/heptane) and crystallization (dichloromethane/hexane) as a yellow solid (162 mg, 66%). MS (ISP) 492.1 [(M+H)$^+$]; mp 277° C.

Example 59

4-{5-[5-(4-Trifluoromethyl-phenyl)-pyrazolo[1,5-a]pyrimidin-3-yl]-[1,2,4]oxadiazol-3-yl}-pyridin-2-ylamine The title compound was prepared from 6-(4-trifluoromethyl-phenyl)-imidazo[1,2-a]pyridine-3-carboxylic acid (example C.23) (154 mg, 0.5 mmol) and 2-amino-N-hydroxy-pyridine-4-carboxamidine (example B.6) (114 mg, 0.75 mmol) according to general procedure II. Obtained after purification by flash chromatography on silica gel (ethyl acetate/heptane) and crystallization (MeOH/dichloromethane/hexane) as a light yellow solid (130 mg, 61%). MS (EI) 423.1 [(M)$^+$]; mp 250° C.

Example 60

4-{5-[8-Methyl-6-(4-trifluoromethyl-phenyl)-imidazo[1,2-a]pyridin-3-yl]-[1,2,4]oxadiazol-3-yl}-pyridin-2-ylamine The title compound was prepared from 8-methyl-6-(4-trifluoromethyl-phenyl)-imidazo[1,2-a]pyridine-3-carboxylic acid (example C.34) (160 mg, 0.5 mmol) and 2-amino-N-hydroxy-pyridine-4-carboxamidine (example B.6) (114 mg, 0.75 mmol) according to general procedure II. Obtained after purification by flash chromatography on silica gel (ethyl acetate/heptane) and crystallization (MeOH/dichloromethane/hexane) as an off-white solid (140 mg, 64%). MS (EI) 436.1 [(M)$^+$]; mp 264° C.

Example 61

4-{5-[6-(4-Trifluoromethyl-phenyl)-imidazo[1,2-a]pyridin-3-yl]-[1,2,4]oxadiazol-3-yl}-pyridin-2-ylamine The title compound was prepared from 6-(4-trifluoromethyl-phenyl)-imidazo[1,2-a]pyridine-3-carboxylic acid (example C.35) (153 mg, 0.5 mmol) and 2-amino-N-hydroxy-pyridine-4-carboxamidine (example B.6) (114 mg, 0.75 mmol) according to general procedure II. Obtained after purification by column chromatography on silica gel (dichloromethane/MeOH 16:1)) and crystallization (MeOH/dichloromethane/hexane) as an off-white solid (80 mg, 38%). MS (EI) 422.9 [(M)$^+$]; mp 280° C.

Example 62

5-{5-[5-(4-Chloro-phenyl)-7-trifluoromethyl-pyrazolo[1,5-a]pyrimidin-3-yl]-[1,2,4]oxadiazol-3-yl}-pyridin-2-ylamine The title compound was prepared from 5-(4-chloro-phenyl)-7-trifluoromethyl-pyrazolo[1,5-a]pyrimidine-3-carboxylic acid (example C.4) (171 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (81 mg, 36%). MS (ISP) 458.1 [(M+H)$^+$]; mp 253° C.

Example 63

5-{5-[5-(4-Chloro-phenyl)-7-difluoromethyl-pyrazolo[1,5-a]pyrimidin-3-yl]-[1,2,4]oxadiazol-3-yl}-pyridin-2-ylamine The title compound was prepared from 5-(4-chloro-phenyl)-7-difluoromethyl-pyrazolo[1,5-a]pyrimidine-3-carboxylic acid (example C.3) (162 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (114 mg, 52%). MS (ISP) 440.2 [(M+H)+]; mp 254° C.

Example 64

5-{5-[5-(4-Chloro-3-methyl-phenyl)-7-trifluoromethyl-pyrazolo[1,5-a]pyrimidin-3-yl]-[1,2,4]oxadiazol-3-yl}-pyridin-2-ylamine The title compound was prepared from 5-(4-chloro-3-methyl-phenyl)-7-trifluoromethyl-pyrazolo[1,5-a]pyrimidine-3-carboxylic acid (example C.6) (178 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (66 mg, 28%). MS (ISP) 471.9 [(M+H)+]; mp 262° C.

Example 65

5-{5-[7-Difluoromethyl-5-(3-methyl-4-trifluoromethyl-phenyl)-pyrazolo[1,5-a]pyrimidin-3-yl]-[1,2,4]oxadiazol-3-yl}-pyridin-2-ylamine The title compound was prepared from 7-difluoromethyl-5-(3-methyl-4-trifluoromethyl-phenyl)-pyrazolo[1,5-a]pyrimidine-3-carboxylic acid (example C.5) (186 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (113 mg, 46%). MS (ISP) 488.1 [(M+H)+]; mp 231° C.

Example 66

5-{5-[5-(3,4-Dichloro-phenyl)-7-difluoromethyl-pyrazolo[1,5-a]pyrimidin-3-yl]-[1,2,4]oxadiazol-3-yl}-pyridin-2-ylamine The title compound was prepared from 5-(3,4-dichloro-phenyl)-7-difluoromethyl-pyrazolo[1,5-a]pyrimidine-3-carboxylic acid (example C.7) (179 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (92 mg, 39%). MS (ISP) 473.9 [(M+H)+]; mp 279° C.

Example 67

5-{5-[5-(3,4-Dichloro-phenyl)-7-trifluoromethyl-pyrazolo[1,5-a]pyrimidin-3-yl]-[1,2,4]oxadiazol-3-yl}-pyridin-2-ylamine The title compound was prepared from 5-(3,4-dichloro-phenyl)-7-trifluoromethyl-pyrazolo[1,5-a]pyrimidine-3-carboxylic acid (example C.9) (188 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (35 mg, 14%). MS (ISP) 492.0 [(M+H)+]; mp 289° C.

Example 68

5-{5-[7-Difluoromethyl-5-(3-ethoxy-4-trifluoromethyl-phenyl)-pyrazolo[1,5-a]pyrimidin-3-yl]-[1,2,4]oxadiazol-3-yl}-pyridin-2-ylamine The title compound was prepared from 7-difluoromethyl-5-(3-ethoxy-4-trifluoromethyl-phenyl)-pyrazolo[1,5-a]pyrimidine-3-carboxylic acid (example C.12) (201 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (110 mg, 43%). MS (ISP) 518.1 [(M+H)+]; mp 250° C.

Example 69

5-{5-[5-(3-Ethoxy-4-trifluoromethyl-phenyl)-7-trifluoromethyl-pyrazolo[1,5-a]pyrimidin-3-yl]-[1,2,4]oxadiazol-3-yl}-pyridin-2-ylamine The title compound was prepared from 5-(3-ethoxy-4-trifluoromethyl-phenyl)-7-trifluoromethyl-pyrazolo[1,5-a]pyrimidine-3-carboxylic acid (example C.11) (210 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (120 mg, 45%). MS (ISP) 536.3 [(M+H)+]; mp 263° C.

Example 70

5-(5-{5-[3-(2,2,2-Trifluoro-ethoxy)-4-trifluoromethyl-phenyl]-7-trifluoromethyl-pyrazolo[1,5-a]pyrimidin-3-yl}-[1,2,4]oxadiazol-3-yl)-pyridin-2-ylamine The title compound was prepared from 5-[3-(2,2,2-trifluoro-ethoxy)-4-trifluoromethyl-phenyl]-7-trifluoromethyl-pyrazolo[1,5-a]pyrimidine-3-carboxylic acid (example C.10) (237 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (129 mg, 44%). MS (ISP) 590.3 [(M+H)+]; mp 284° C.

Example 71

5-(5-{7-Difluoromethyl-5-[3-(2,2,2-trifluoro-ethoxy)-4-trifluoromethyl-phenyl]-pyrazolo[1,5-a]pyrimidin-3-yl}-[1,2,4]oxadiazol-3-yl)-pyridin-2-ylamine The title compound was prepared from 7-difluoromethyl-5-[3-(2,2,2-trifluoro-ethoxy)-4-trifluoromethyl-phenyl]-pyrazolo[1,5-a]pyrimidine-3-carboxylic acid (example C.14) (228 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by

Example 72

5-{5-[5-(3-Chloro-4-trifluoromethyl-phenyl)-7-difluoromethyl-pyrazolo[1,5-a]pyrimidin-3-yl]-[1,2,4]oxadiazol-3-yl}-pyridin-2-ylamine The title compound was prepared from 5-(3-chloro-4-trifluoromethyl-phenyl)-7-difluoromethyl-pyrazolo[1,5-a]pyrimidine-3-carboxylic acid (example C.15) (196 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (97 mg, 38%). MS (ISP) 508.2 [(M+H)$^+$]; mp 252° C.

Example 73

5-{5-[5-(3-Chloro-4-trifluoromethyl-phenyl)-7-trifluoromethyl-pyrazolo[1,5-a]pyrimidin-3-yl]-[1,2,4]oxadiazol-3-yl}-pyridin-2-ylamine The title compound was prepared from 5-(3-chloro-4-trifluoromethyl-phenyl)-7-trifluoromethyl-pyrazolo[1,5-a]pyrimidine-3-carboxylic acid (example C.17) (205 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (90 mg, 34%). MS (ISP) 526.1 [(M+H)$^+$]; mp 234° C.

Example 74

5-{5-[7-Difluoromethyl-5-(3-fluoro-4-trifluoromethyl-phenyl)-pyrazolo[1,5-a]pyrimidin-3-yl]-[1,2,4]oxadiazol-3-yl}-pyridin-2-ylamine The title compound was prepared from 7-difluoromethyl-5-(3-fluoro-4-trifluoromethyl-phenyl)-pyrazolo[1,5-a]pyrimidine-3-carboxylic acid (example C.16) (188 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (86 mg, 35%). MS (EI) 491.1 [(M)$^+$]; mp 242° C.

Example 75

5-{5-[5-(3-Fluoro-4-trifluoromethyl-phenyl)-7-trifluoromethyl-pyrazolo[1,5-a]pyrimidin-3-yl]-[1,2,4]oxadiazol-3-yl}-pyridin-2-ylamine The title compound was prepared from 5-(3-fluoro-4-trifluoromethyl-phenyl)-7-trifluoromethyl-pyrazolo[1,5-a]pyrimidine-3-carboxylic acid (example C.18) (197 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (95 mg, 37%). MS (ISP) 510.3 [(M+H)$^+$]; mp 233° C.

Example 76

5-{5-[5-(3,4-Difluoro-phenyl)-7-trifluoromethyl-pyrazolo[1,5-a]pyrimidin-3-yl]-[1,2,4]oxadiazol-3-yl}-pyridin-2-ylamine The title compound was prepared from 5-(3,4-difluoromethyl-phenyl)-7-trifluoromethyl-pyrazolo[1,5-a]pyrimidine-3-carboxylic acid (example C.21) (172 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (97 mg, 42%). MS (EI) 459.1 [(M)$^+$]; mp 262° C.

Example 77

5-{5-[5-(4-Chloro-3-methyl-phenyl)-7-difluoromethyl-pyrazolo[1,5-a]pyrimidin-3-yl]-[1,2,4]oxadiazol-3-yl}-pyridin-2-ylamine The title compound was prepared from 5-(4-chloro-3-methyl-phenyl)-7-difluoromethyl-pyrazolo[1,5-a]pyrimidine-3-carboxylic acid (example C.13) (169 mg, 0.5 mmol) and 6-amino-N-hydroxy-nicotinamidine (example B.4) (114 mg, 0.75 mmol) according to general procedure II. Obtained after flash chromatography on silica gel (ethyl acetate/heptane) and further purification by crystallization (dichloromethane/hexane) as a yellow solid (68 mg, 30%). MS (EI) 453.0 [(M)$^+$]; mp 243° C.

Example 78

5-{5-[5-(3,4-Difluoro-phenyl)-7-trifluoromethyl-pyrazolo[1,5-a]pyrimidin-3-yl]-[1,2,4]oxadiazol-3-yl}-pyrimidin-2-ylamine The title compound was prepared from 5-(3,4-difluoromethyl-phenyl)-7-trifluoromethyl-pyrazolo[1,5-a]pyrimidine-3-carboxylic acid (example C.21) (172 mg, 0.5 mmol) and 2-amino-N-hydroxy-pyrimidine-5-carboxamidine (example B.5) (115 mg, 0.75 mmol) according to general procedure II. Obtained after flash chromatography on silica gel (ethyl acetate/heptane) and further purification by crystallization (dichloromethane/hexane) as a yellow solid (130 mg, 56%). MS (EI) 460.1 [(M)$^+$]; mp 268° C.

Example 79

5-{5-[5-(3-Fluoro-4-trifluoromethyl-phenyl)-7-trifluoromethyl-pyrazolo[1,5-a]pyrimidin-3-yl]-[1,2,4]oxadiazol-3-yl}-pyrimidin-2-ylamine The title compound was prepared from 5-(3-fluoro-4-trifluoromethyl-phenyl)-7-trifluoromethyl-pyrazolo[1,5-a]pyrimidine-3-carboxylic acid (example C.18) (197 mg, 0.5 mmol) and 2-amino-N-hydroxy-pyrimidine-5-carboxamidine (example B.5) (115 mg, 0.75 mmol) according to general procedure II. Obtained after flash chromatography on silica gel (ethyl acetate/heptane) and further purification by crystallization (dichloromethane/hexane) as a yellow solid (130 mg, 51%). MS (EI) 510.1 [(M)$^+$]; mp 270° C.

--- crystallization (dichloromethane/hexane) as a yellow solid (125 mg, 44%). MS (ISP) 572.1 [(M+H)$^+$]; mp 285° C.

Example 80

5-{5-[5-(3-Chloro-4-trifluoromethyl-phenyl)-7-trifluoromethyl-pyrazolo[1,5-a]pyrimidin-3-yl]-[1,2,4]oxadiazol-3-yl}-pyrimidin-2-ylamine The title compound was prepared from 5-(3-chloro-4-trifluoromethyl-phenyl)-7-trifluoromethyl-pyrazolo[1,5-a]pyrimidine-3-carboxylic acid (example C.17) (205 mg, 0.5 mmol) and 2-amino-N-hydroxy-pyrimidine-5-carboxamidine (example B.5) (115 mg, 0.75 mmol) according to general procedure II. Obtained after flash chromatography on silica gel (ethyl acetate/heptane) and further purification by crystallization (dichloromethane/hexane) as a yellow solid (150 mg, 57%). MS (EI) 526.1 [(M)$^+$]; mp 279° C.

Example 81

5-{5-[5-(3,4-Dichloro-phenyl)-7-trifluoromethyl-pyrazolo[1,5-a]pyrimidin-3-yl]-[1,2,4]oxadiazol-3-yl}-pyrimidin-2-ylamine The title compound was prepared from 5-(3,4-dichloro-phenyl)-7-trifluoromethyl-pyrazolo[1,5-a]pyrimidine-3-carboxylic acid (example C.9) (188 mg, 0.5 mmol) and 2-amino-N-hydroxy-pyrimidine-5-carboxamidine (example B.5) (115 mg, 0.75 mmol) according to general procedure II. Obtained after flash chromatography on silica gel (ethyl acetate/heptane) and further purification by crystallization (dichloromethane/hexane) as a yellow solid (180 mg, 73%). MS (EI) 492.0 [(M)$^+$]; mp 300° C.

Example 82

5-{5-[5-(4-Chloro-phenyl)-7-trifluoromethyl-pyrazolo[1,5-a]pyrimidin-3-yl]-[1,2,4]oxadiazol-3-yl}-pyrimidin-2-ylamine The title compound was prepared from 5-(4-chloro-phenyl)-7-trifluoromethyl-pyrazolo[1,5-a]pyrimidine-3-carboxylic acid (example C.4) (171 mg, 0.5 mmol) and 2-amino-N-hydroxy-pyrimidine-5-carboxamidine (example B.5) (115 mg, 0.75 mmol) according to general procedure II. Obtained after flash chromatography on silica gel (ethyl acetate/heptane) and further purification by crystallization (dichloromethane/hexane) as a yellow solid (165 mg, 72%). MS (EI) 458.1 [(M)$^+$]; mp 268° C.

Example 83

5-{5-[5-(3-Methyl-4-trifluoromethyl-phenyl)-7-trifluoromethyl-pyrazolo[1,5-a]pyrimidin-3-yl]-[1,2,4]oxadiazol-3-yl}-pyrimidin-2-ylamine The title compound was prepared from 5-(3-methyl-4-trifluoromethyl-phenyl)-7-trifluoromethyl-pyrazolo[1,5-a]pyrimidine-3-carboxylic acid (example C.8) (195 mg, 0.5 mmol) and 2-amino-N-hydroxy-pyrimidine-5-carboxamidine (example B.5) (115 mg, 0.75 mmol) according to general procedure II. Obtained after purification by flash chromatography (ethyl acetate/heptane) and crystallization (dichloromethane/hexane) as a yellow solid (143 mg, 56%). MS (EI) 506.1 [(M)$^+$]; mp 272° C.

Example 84

5-{5-[5-(4-Chloro-3-methyl-phenyl)-7-trifluoromethyl-pyrazolo[1,5-a]pyrimidin-3-yl]-[1,2,4]oxadiazol-3-yl}-pyrimidin-2-ylamine The title compound was prepared from 5-(4-chloro-3-methyl-phenyl)-7-trifluoromethyl-pyrazolo[1,5-a]pyrimidine-3-carboxylic acid (example C.6) (178 mg, 0.5 mmol) and 2-amino-N-hydroxy-pyrimidine-5-carboxamidine (example B.5) (115 mg, 0.75 mmol) according to general procedure II. Obtained after flash chromatography on silica gel (ethyl acetate/heptane) and further purification by crystallization (dichloromethane/hexane) as a yellow solid (54 mg, 23%). MS (EI) 472.1 [(M)$^+$]; mp 272° C.

Example 85

4-{5-[5-(4-Chloro-phenyl)-7-trifluoromethyl-pyrazolo[1,5-a]pyrimidin-3-yl]-[1,2,4]oxadiazol-3-yl}-pyridin-2-ylamine The title compound was prepared from 5-(4-chloro-phenyl)-7-trifluoromethyl-pyrazolo[1,5-a]pyrimidine-3-carboxylic acid (example C.4) (171 mg, 0.5 mmol) and 2-amino-N-hydroxy-pyridine-4-carboxamidine (example B.6) (114 mg, 0.75 mmol) according to general procedure II. Obtained after trituration with water and further purification by crystallization (dichloromethane/hexane) as a yellow solid (112 mg, 49%). MS (EI) 457.1 [(M)$^+$]; mp 252° C.

Example 86

4-{5-[5-(3,4-Dichloro-phenyl)-7-trifluoromethyl-pyrazolo[1,5-a]pyrimidin-3-yl]-[1,2,4]oxadiazol-3-yl}-pyridin-2-ylamine The title compound was prepared from 5-(3,4-chloro-phenyl)-7-trifluoromethyl-pyrazolo[1,5-a]pyrimidine-3-carboxylic acid (example C.9) (188 mg, 0.5 mmol) and 2-amino-N-hydroxy-pyridine-4-carboxamidine (example B.6) (114 mg, 0.75 mmol) according to general procedure II. Obtained after trituration with water and further purification by crystallization (dichloromethane/hexane) as a yellow solid (149 mg, 61%). MS (EI) 491.0 [(M)$^+$]; mp 262° C.

Example 87

4-{5-[5-(3-Methyl-4-trifluoromethyl-phenyl)-7-trifluoromethyl-pyrazolo[1,5-a]pyrimidin-3-yl]-[1,2,4]oxadiazol-3-yl}-pyridine-2-ylamine The title compound was prepared from 5-(3-methyl-4-trifluoromethyl-phenyl)-7-trifluoromethyl-pyrazolo[1,5-a]pyrimidine-3-carboxylic acid (example C.8) (195 mg, 0.5 mmol) and 2-amino-N-hydroxy-pyridine-4-carboxamidine (example B.6) (114 mg, 0.75 mmol) according to general procedure II. Obtained after trituration with water and further purification by crystallization (dichloromethane/hexane) as a yellow solid (167 mg, 66%). MS (EI) 505.2 [(M)$^+$]; mp 245° C.

Preparation of Pharmaceutical Compositions Comprising Compounds of the Invention

Example I

Tablets of the following composition are produced in a conventional manner:

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example II

Tablets of the following composition are produced in a conventional manner:

|  | mg/Tablet |
| --- | --- |
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

Example III

Capsules of the following composition are produced:

|  | mg/Capsule |
| --- | --- |
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:
1. A compound of formula (I):

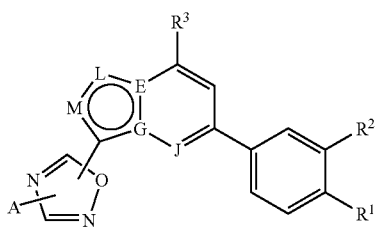

(I)

wherein
L and G are N, E is C, and J and M are CH;

$R^1$ and $R^2$ are each independently H, halogen, $C_{1-6}$-alkyl optionally substituted by one or more F or $C_{1-6}$-alkoxy, or $C_{1-6}$-alkoxy optionally substituted by one or more F;

$R^3$ is H, —C(CH$_3$)$_2$OH, or linear $C_{1-4}$-alkyl or $C_{3-4}$-cycloalkyl each of the latter three is optionally substituted by one or more substituent(s) selected from the group consisting of 1 to 6 F and 1 to 2 OH;

A is selected from the group consisting of aryl and 5 or 6-membered heteroaryl each of which is optionally substituted by one to four $R^a$;

$R^a$ is F, OH, amino, $C_{1-6}$-alkyl optionally substituted by OH, $C_{1-6}$-alkoxy, $C_{3-4}$-cycloalkyl, —CO—$R^b$, SO$_2$—$R^c$ or SO$_2$—NR$^d$R$^e$;

$R^b$ is amino;

$R^c$ is OH or $C_{1-6}$-alkyl;

$R^d$ and $R^e$ can be the same or different and are selected from the group consisting of:
H;
straight or branched $C_{1-6}$-alkyl optionally substituted by one or more substituent(s) selected from the group consisting of F, cyano, OH, di($C_{1-6}$-alkyl)amino, $C_{3-6}$-cycloalkyl, 5 or 6-membered heterocycloalkyl, aryl and 5 or 6-membered heteroaryl;
$C_{3-6}$-cycloalkyl;
aryl; and
5 or 6-membered heteroaryl;
or $R^d$ and $R^e$ together with the nitrogen atom to which they are attached, form a heterocyclic ring of 4 to 6 ring members which is optionally substituted by OH or $C_{1-6}$-alkyl;

or a pharmaceutically acceptable salt thereof.

2. A compound of claim 1 having formula (I-b):

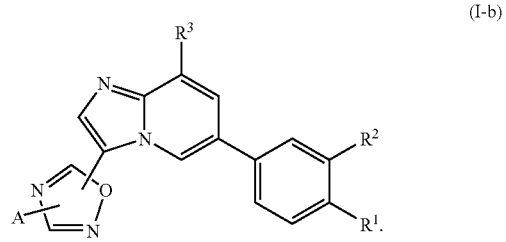

(I-b)

3. The compound of claim 2, wherein:
$R^1$ is halo or CF$_3$;
$R^2$ is H, halo, or $C_{1-6}$-alkyl $C_{1-6}$-alkoxy each of the latter three is optionally substituted by one or more F;
$R^3$ is H, linear $C_{1-4}$-alkyl, or $C_{3-4}$-cycloalkyl each of the latter two is optionally substituted by 1 to 6 F;
A is selected from the group consisting of aryl and 5 or 6-membered heteroaryl each of which is optionally substituted by one to four $R^a$;
$R^a$ is amino or SO$_2$—NR$^d$R$^e$; wherein $R^d$ and $R^e$ are each H;
or a pharmaceutically acceptable salt thereof.

4. The compound of claim 3, wherein:
$R^1$ is Cl, F or CF$_3$;
$R^2$ is H, F, methyl, OEt, CHF$_2$, CF$_3$, OCF$_3$ or OCH$_2$CF$_3$;
$R^3$ is H, methyl or cyclopropyl, each of the latter two is optionally substituted by 2 or 3 F;
A is selected from the group consisting of phenyl, thiophenyl, pyridinyl, pyrimidinyl and pyrazolyl, each of which is optionally substituted by one $R^a$;
$R^a$ is amino or SO$_2$—NR$^d$R$^e$; wherein $R^d$ and $R^e$ are each H;
or a pharmaceutically acceptable salt thereof.

5. The compound of claim 4, selected from the group consisting of:
- 3-{5-[8-Trifluoromethyl-6-(4-trifluoromethyl-phenyl)-imidazo[1,2-a]pyridin-3-yl]-[1,2,4]oxadiazol-3-yl}-benzenesulfonamide;
- 4-{5-[8-Trifluoromethyl-6-(4-trifluoromethyl-phenyl)-imidazo[1,2-a]pyridin-3-yl]-[1,2,4]oxadiazol-3-yl}-benzenesulfonamide;
- 4-{5-[6-(4-Chloro-phenyl)-8-methyl-imidazo[1,2-a]pyridin-3-yl]-[1,2,4]oxadiazol-3-yl}-benzenesulfonamide;
- 3-{5-[6-(4-Chloro-phenyl)-8-methyl-imidazo[1,2-a]pyridin-3-yl]-[1,2,4]oxadiazol-3-yl}-benzenesulfonamide;
- 5-{5-[6-(4-Chloro-phenyl)-8-methyl-imidazo[1,2-a]pyridin-3-yl]-[1,2,4]oxadiazol-3-yl}-thiophene-2-sulfonic acid amide;
- 4-{5-[8-Methyl-6-(4-trifluoromethyl-phenyl)-imidazo[1,2-a]pyridin-3-yl]-[1,2,4]oxadiazol-3-yl}-benzenesulfonamide;
- 3-{5-[8-Methyl-6-(4-trifluoromethyl-phenyl)-imidazo[1,2-a]pyridin-3-yl]-[1,2,4]oxadiazol-3-yl}-benzenesulfonamide;
- 5-{5-[8-Methyl-6-(4-trifluoromethyl-phenyl)-imidazo[1,2-a]pyridin-3-yl]-[1,2,4]oxadiazol-3-yl}-thiophene-2-sulfonic acid amide; and
- 5-{5-[8-Methyl-6-(4-trifluoromethyl-phenyl)-imidazo[1,2-a]pyridin-3-yl]-[1,2,4]oxadiazol-3-yl}-pyridin-2-ylamine.

6. The compound of claim 4, selected from the group consisting of:
- 5-{5-[8-Methyl-6-(4-trifluoromethyl-phenyl)-imidazo[1,2-a]pyridin-3-yl]-[1,2,4]oxadiazol-3-yl}-pyrimidin-2-ylamine;
- 4-{5-[6-(4-Trifluoromethyl-phenyl)-imidazo[1,2-a]pyridin-3-yl]-[1,2,4]oxadiazol-3-yl}-benzenesulfonamide;
- 3-{5-[6-(4-Trifluoromethyl-phenyl)-imidazo[1,2-a]pyridin-3-yl]-[1,2,4]oxadiazol-3-yl}-benzenesulfonamide;
- 5-{5-[6-(4-Trifluoromethyl-phenyl)-imidazo[1,2-a]pyridin-3-yl]-[1,2,4]oxadiazol-3-yl}-thiophene-2-sulfonic acid amide;
- 5-{5-[6-(4-Chloro-phenyl)-imidazo[1,2-a]pyridin-3-yl]-[1,2,4]oxadiazol-3-yl}-thiophene-2-sulfonic acid amide;
- 5-{5-[6-(4-Trifluoromethyl-phenyl)-imidazo[1,2-a]pyridin-3-yl]-[1,2,4]oxadiazol-3-yl}-pyridin-2-ylamine;
- 5-{5-[6-(4-Chloro-phenyl)-imidazo[1,2-a]pyridin-3-yl]-[1,2,4]oxadiazol-3-yl}-pyridin-2-ylamine;
- 4-{5-[8-Methyl-6-(4-trifluoromethyl-phenyl)-imidazo[1,2-a]pyridin-3-yl]-[1,2,4]oxadiazol-3-yl}-pyridin-2-ylamine; and
- 4-{5-[6-(4-Trifluoromethyl-phenyl)-imidazo[1,2-a]pyridin-3-yl]-[1,2,4]oxadiazol-3-yl}-pyridin-2-ylamine.

7. The compound of claim 1, wherein A is aryl optionally substituted by one to four $R^a$.

8. The compound of claim 1, wherein A is a 5 or 6-membered heteroaryl optionally substituted by one to four $R^a$.

9. The compound of claim 1, wherein $R^d$ and $R^e$ are each independently H;
straight or branched $C_{1-6}$-alkyl optionally substituted by one or more substituent(s) selected from the group consisting of F, cyano, OH, di($C_{1-6}$-alkyl)amino, and $C_{3-6}$-cycloalkyl; or
$C_{3-6}$-cycloalkyl.

10. The compound of claim 1, wherein one of $R^d$ and $R^e$ is straight or branched $C_{1-6}$-alkyl optionally substituted by one or more substituent(s) selected from the group consisting of 5 or 6-membered heterocycloalkyl, aryl and 5 or 6-membered heteroaryl.

11. The compound of claim 1, wherein one of $R^d$ and $R^e$ is aryl.

12. The compound of claim 1, wherein one of $R^d$ and $R^e$ is a 5 or 6-membered heteroaryl.

13. The compound of claim 1, wherein $R^d$ and $R^e$, together with the nitrogen atom to which they are attached, form a heterocyclic ring of 4 to 6 ring members which is optionally substituted by OH or $C_{1-6}$-alkyl.

* * * * *